United States Patent
Hunt et al.

(10) Patent No.: US 10,624,643 B2
(45) Date of Patent: Apr. 21, 2020

(54) ELONGATED TISSUE COMPRESSION DEVICE SYSTEM WITH SMOOTH OUTER CONTOUR AND ORTHOGONAL CURVED ALIGNING SURFACES

(71) Applicant: ETHICON LLC, Guaynabo, PR (US)

(72) Inventors: John V. Hunt, Cincinnati, OH (US);
Daniel W. Price, Loveland, OH (US);
Nicholas B. Van Stolk, Cincinnati, OH (US); Gregory J. Bakos, Mason, OH (US); Bethany F. Grant, Scituate, MA (US)

(73) Assignee: Ethicon LLC, Guaynabo, PR (US)

( * ) Notice: Subject to any disclaimer, the term of this patent is extended or adjusted under 35 U.S.C. 154(b) by 416 days.

(21) Appl. No.: 15/419,132

(22) Filed: Jan. 30, 2017

(65) Prior Publication Data

US 2018/0214149 A1      Aug. 2, 2018

(51) Int. Cl.
*A61B 17/11*      (2006.01)
*A61B 17/00*      (2006.01)

(52) U.S. Cl.
CPC ........... *A61B 17/11* (2013.01); *A61B 17/1114* (2013.01); *A61B 2017/00876* (2013.01);
(Continued)

(58) Field of Classification Search
CPC . A61B 17/11; A61B 17/1114; A61B 17/1117; A61B 17/0487;
(Continued)

(56) References Cited

U.S. PATENT DOCUMENTS 5,667,526 A * 9/1997 Levin ................... A61B 17/282
606/151
8,142,454 B2   3/2012 Harrison et al.
(Continued)

FOREIGN PATENT DOCUMENTS

WO      WO 97/27898 A1    8/1997
WO      WO 2007/101526 A1   9/2007

OTHER PUBLICATIONS

International Search Report and Written Opinion dated Apr. 9, 2018 for Application No. PCT/IB2018/050353, 13 pgs.
(Continued)

*Primary Examiner* — Diane D Yabut
(74) *Attorney, Agent, or Firm* — Frost Brown Todd LLC

(57) ABSTRACT

An exemplary tissue compression device for forming an anastomosis between first and second anatomical structures includes a first device portion having a first mating surface, and a second device portion having a second mating surface configured to mate with the first mating surface to compress tissue positioned therebetween. Each of the first and second mating surfaces includes a contoured portion, and the contoured portions are configured to mate with one another to facilitate alignment of the first and second device portions. A first one of the contoured portions may be formed with a concave contour and a second one of the contoured portions may be formed with a complementary convex contour. The device portions may further include first and second magnetic members configured to draw the device portions together to engage the first mating surface with the second mating surface.

19 Claims, 20 Drawing Sheets

(52) U.S. Cl.
CPC .............. *A61B 2017/1117* (2013.01); *A61B 2017/1139* (2013.01)

(58) Field of Classification Search
CPC .. A61B 2017/1139; A61B 2017/00876; A61B 2017/0456; A61B 2017/0458; F16G 11/105; F16G 11/106
See application file for complete search history.

(56) References Cited

U.S. PATENT DOCUMENTS

| | | |
|---|---|---|
| 8,518,062 B2 | 8/2013 | Cole et al. |
| 8,623,036 B2 | 1/2014 | Harrison et al. |
| 9,364,238 B2 | 6/2016 | Bakos et al. |
| 2002/0143347 A1* | 10/2002 | Cole .................... H01F 41/026 606/153 |
| 2010/0063520 A1* | 3/2010 | Bilotti ................. A61B 17/1114 606/153 |

OTHER PUBLICATIONS

U.S. Appl. No. 15/298,816, filed Oct. 20, 2016.
U.S. Appl. No. 15/419,086, filed Jan. 30, 2017.
U.S. Appl. No. 15/419,102, filed Jan. 30, 2017.
U.S. Appl. No. 15/419,151, filed Jan. 30, 2017.
U.S. Appl. No. 61/967,845, filed Sep. 7, 2012.

* cited by examiner

ELONGATED TISSUE COMPRESSION DEVICE SYSTEM WITH SMOOTH OUTER CONTOUR AND ORTHOGONAL CURVED ALIGNING SURFACES

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298,816, entitled "Method for Partial Diversion of the Intestinal Tract," filed Oct. 20, 2016, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements, and in which:

Figure 1:
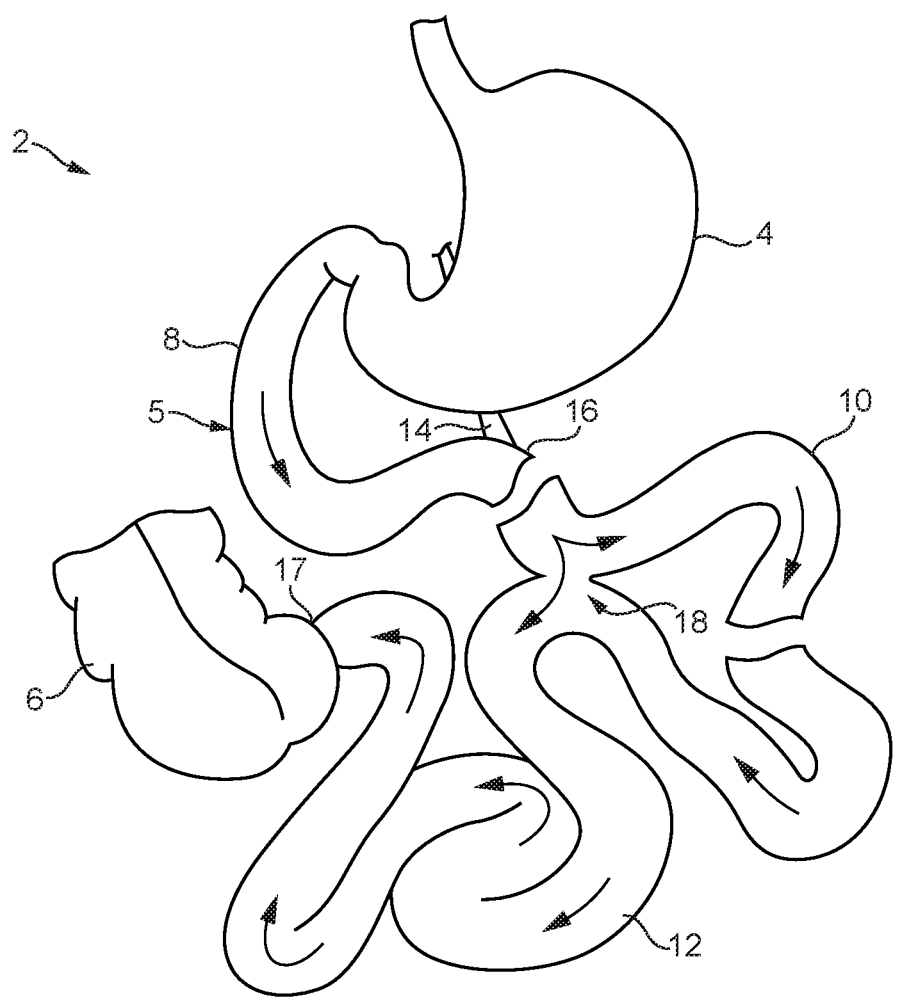
FIG. 1 depicts a diagrammatic view of a portion of a patient's digestive system, showing an exemplary side-by-side anastomosis formed in the small intestine.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY INTESTINAL ANASTOMOSIS

As noted above, it may be desirable to provide an anastomosis between two anatomical structures within a patient's body, such as two portions of a patient's gastrointestinal tract. FIG. 1 shows an exemplary portion of a gastrointestinal tract (2) including, in downstream order, a stomach (4), a small intestine (5), and a large intestine (6). The small intestine (5) is subdivided into three portions: the duodenum (8), the jejunum (10), and the ileum (12), listed in downstream order. The duodenum (8) is supported by a suspensory muscle (14) known as the ligament of Treitz, and transitions into the jejunum (10) at the duodenojejunal flexure (16). The ileum (12) transitions into the large intestine (6) at the ileocecal junction (17), also known as the ileocecal valve.

Figure 2:
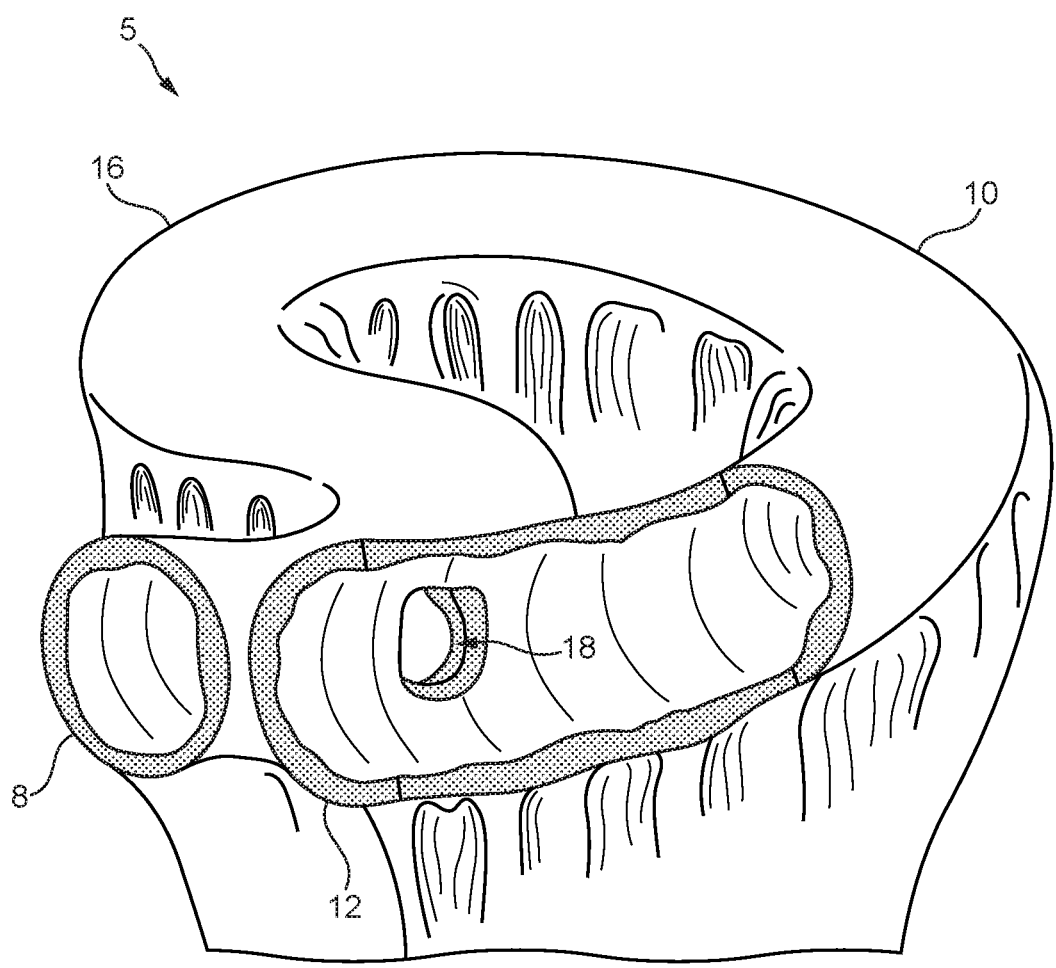
FIG. 2 depicts a partial perspective view of another exemplary side-by-side anastomosis formed in the small intestine.

The gastrointestinal tract (2) is shown including an exemplary anastomosis (18) formed between a proximal portion of the jejunum (10) and the ileum (12). The anastomosis (18) has an inlet side formed through a sidewall of the jejunum (10) at a location adjacent to and downstream of the duodenojejunal flexure (16) and the ligament of Treitz (14). The anastomosis (18) additionally has an outlet side formed through a sidewall of the ileum (12). It will be appreciated that the anastomosis (18) may be positioned at various other suitable locations along the gastrointestinal tract (2). For example, as shown in FIG. 2, the anastomosis (18) may be formed between the duodenum (8) and the ileum (12). Additional exemplary locations of the anastomosis (18) are described in U.S. patent application Ser. No. 15/298,816, entitled "Methods for Partial Diversion of the Intestinal Tract," filed Oct. 20, 2016, the disclosure of which is hereby incorporated by referenced herein. It will be further appreciated that the anastomosis (18) may be located elsewhere within a patient's body, other than within the gastrointestinal tract (2). In that regard, it will be understood that the exemplary tissue compression devices shown and described herein may be employed to create anastomoses in various other bodily organs having an internal lumen, and thus are not limited to use in a patient's gastrointestinal tract (2).

Still referring to FIG. 1, the exemplary anastomosis (18) shown provides a pathway for direct fluid communication between the proximal portion of the patient's jejunum (10) and the ileum (12), thereby bypassing a majority of the jejunum (10), located downstream. Consequently, chyme exiting the stomach (4) may flow directly through the duodenum (8), then through the proximal portion of the jejunum (10) and directly into the ileum (12), via the anastomosis (18), without passing through the downstream portion of the jejunum (10). In some instances, a first portion of the chyme exiting the stomach (4) may flow directly from the proximal portion of the jejunum (10) to the ileum (12), via the anastomosis (18). Simultaneously, a second portion of the chyme may pass the anastomosis (18) and flow through the downstream portion of the jejunum (10), rejoining with the first portion of chyme in the ileum (12) before passing into the large intestine (6). Accordingly, the anastomosis (18) may provide a complete diversion or a partial diversion of chyme passing through the jejunum (10).

Forming a side-by-side anastomosis (18) between two portions of the gastrointestinal tract (2), positioned adjacent to one another, may be achieved using a compression device having first and second device portions that clamp intestinal tissue therebetween, as described above. In some procedures, the device portions may be introduced into the intestinal lumen via two or more enterotomies formed in the intestinal sidewalls at respective upstream and downstream locations. In other procedures, the device portions may be introduced into the intestinal lumen endoscopically, using two or more endoscopes inserted through naturally occurring body orifices and directed into the intestinal lumen from opposing directions. The exemplary tissue compression devices disclosed herein may be positioned within a patient using either of these methods, for example.

II. EXEMPLARY ANASTOMOSIS TISSUE COMPRESSION DEVICE HAVING CONTOURED MATING SURFACES

As will be described in greater detail below, the first and second device portions of the tissue compression devices disclosed herein may include magnetic members that draw the device portions together. The device portions, when drawn together magnetically, compress tissue positioned therebetween with a clamping force sufficient to cause ischemia and eventual necrosis of the tissue. Once necrosis occurs, the device falls away to reveal an anastomosis, and the device is then passed downstream through the gastrointestinal tract (2).

It should be understood that it may be desirable to provide contoured edges in a tissue compression device that is used to form an anastomosis. Such contoured edges may provide better tissue shaping than the tissue shaping that would otherwise be provided by sharp edges. Moreover, smooth mating surfaces in a tissue compression device may reduce the likelihood that tissue captured between the surfaces will interfere with the mating of such surfaces. Several exemplary configurations that provide contoured edges and smooth mating surfaces are described in greater detail below.

Figure 3:
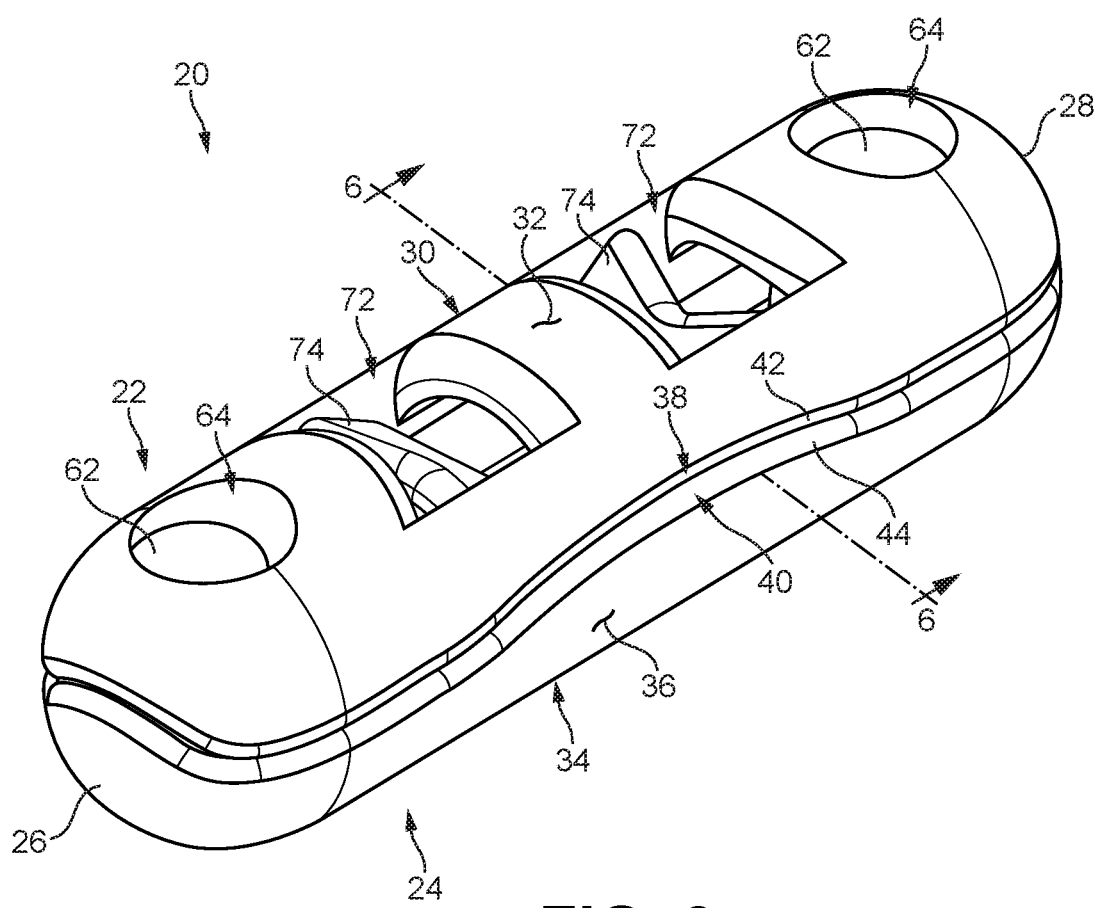
FIG. 3 depicts a perspective view of an exemplary tissue compression device for forming an anastomosis.

A. Structural Features of Exemplary Tissue Compression Device Having Contoured Mating Surfaces FIGS. 3-4B show an exemplary tissue compression device (20) for forming an anastomosis, such as a side-by-side anastomosis, in an assembled configuration. The tissue compression device (20) includes a first device half (22) and a second device half (24) that mate together to define an elongate device body that extends along a longitudinal device axis between a convexly rounded first end (26) and a convexly rounded second end (28). The first device half (22) includes a first rigid body (30) having a rounded outer periphery (32), and the second device half (24) includes a second rigid body (34) having a rounded outer periphery (36). Each of the rigid bodies (30, 34) may be formed as a unitary structure having a length, measured along the device axis, that is greater than its width, measured transverse to the device axis. Accordingly, when the device halves (22, 24) mate together, as shown in FIG. 3, they define a device body having a fully rounded outer periphery and a length that is greater than its width so as to define an elongate, low-profile, pill-shaped structure.

Figure 4A:
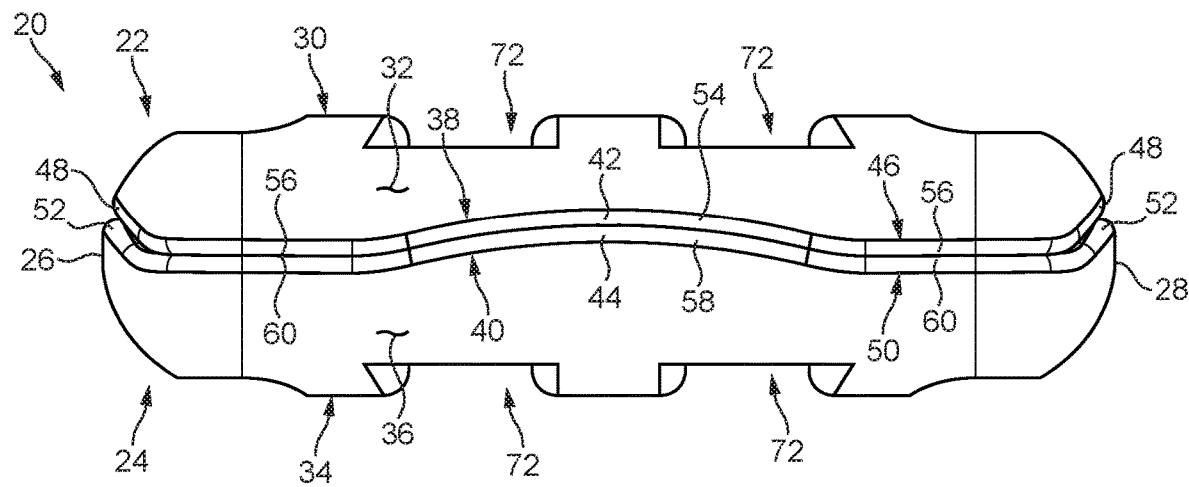
FIG. 4A depicts a side elevational view of the tissue compression device of FIG. 3.
Figure 4B:
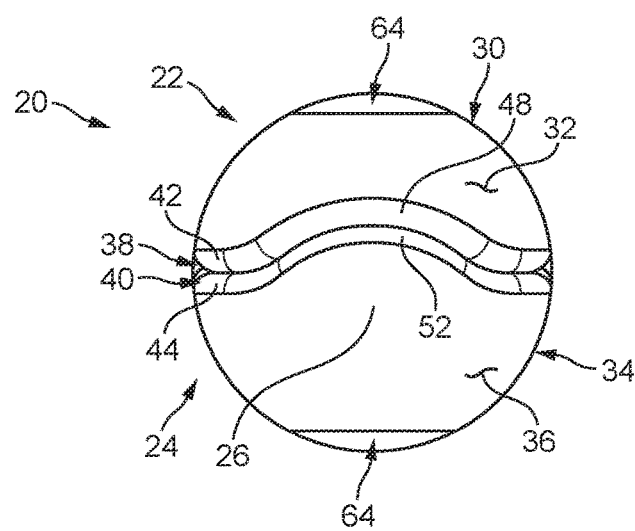
FIG. 4B depicts an end elevational view of the tissue compression device of FIG. 3.

As best shown in FIGS. 4A and 4B, the tissue compression device (20) may be formed with a transverse cross-section having a rounded shape to provide the device (20) with a rounded and smooth outer periphery that is atraumatic to patient tissue. As best shown in FIG. 4B, the exemplary device (20) is formed with a generally circular shaped cross-section. Additionally, as shown in FIG. 4A, the circular cross-section may be uniform in diameter along a medial portion of the device (20) extending between its first and second rounded ends (26, 28). In alternative versions, the device (20) may be formed with a transverse cross-section of various other shapes, such as various rounded shapes, and the cross-section may be uniform or non-uniform (e.g., tapered) along a length of the device (20).

Figure 5:
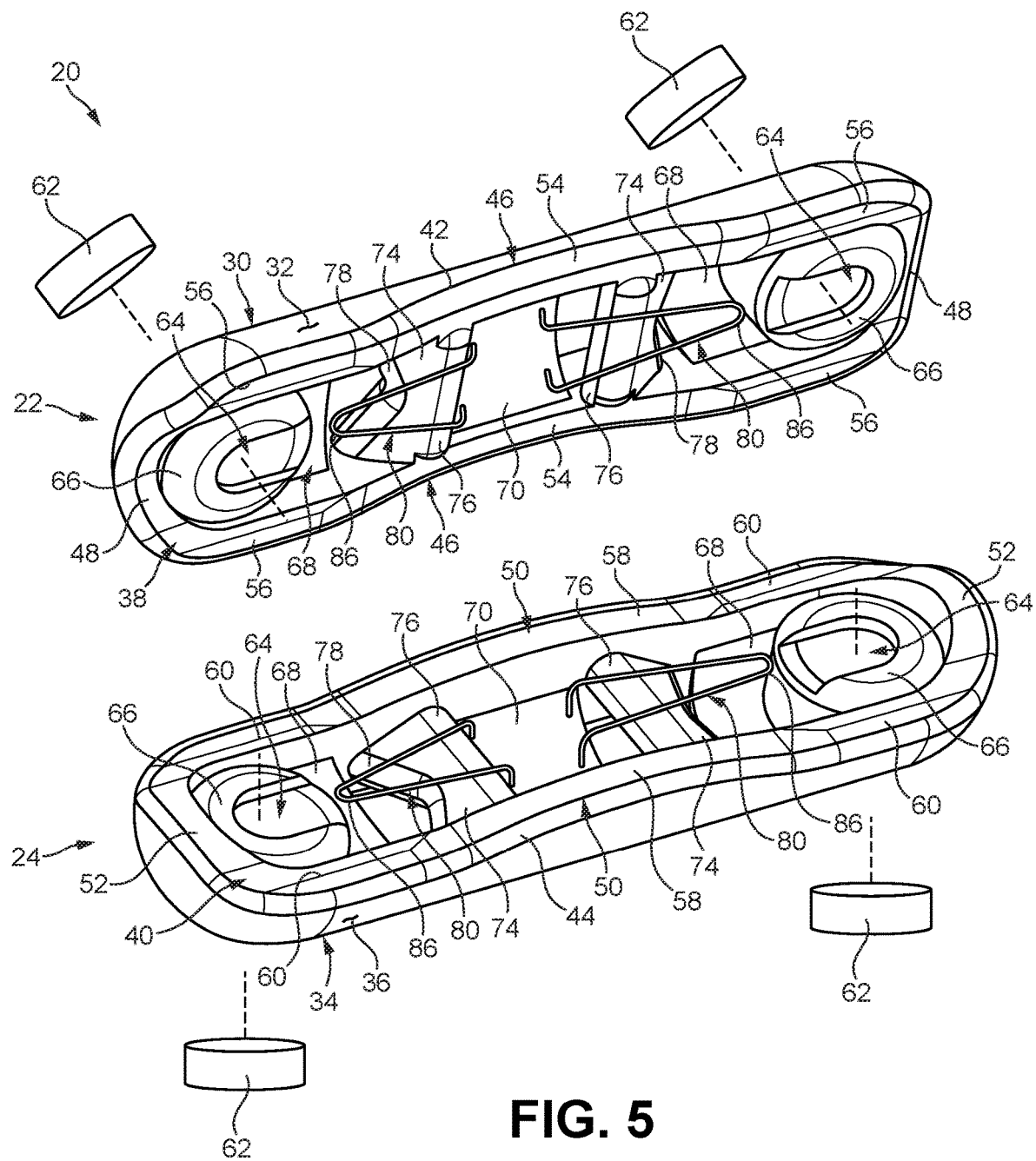
FIG. 5 depicts a disassembled perspective view of the tissue compression device of FIG. 3.

FIG. 5 shows the device (20) in a disassembled configuration to reveal additional structural features. For illustrative purposes only, the first device half (22) is shown in an upper position and the second device half (24) is shown in a lower position. In that regard, it will be appreciated that relative positional terms including "upper," "lower" and similar terms as may be used herein are illustrative only and are not limiting of the features to which they refer nor of the various orientations in which the device (20) may be employed.

As best shown in FIGS. 4A-5, the first device half (22) includes a first mating surface (38) that extends continuously about a perimeter of the mating side of the first device half (22). Similarly, the second device half (24) includes a second mating surface (40) that extends continuously about a perimeter of the mating side of the second device half (24). Each mating surface (38, 40) includes a rounded outer edge (42, 44) that transitions smoothly to the rounded outer periphery (32, 36) of the respective device half (22, 24). In the example shown, the first mating surface (38) includes a pair of elongate side portions (46) extending generally parallel to the device axis; and a pair of concave end portions (48) extending generally transverse to the device axis and arranged at the ends of the side portions (46). The second mating surface (40) includes a corresponding pair of elongate side portions (50) extending generally parallel to the device axis; and a corresponding pair of convex end portions (52) extending generally transverse to the device axis and arranged at the ends of the side portions (50).

The first and second mating surfaces (38, 40) are shaped with complementary contours that facilitate alignment of the device halves (22, 24) with one another, and enable the device halves (22, 24) to mate together in contacting engagement along the full length of the mating surfaces (38, 40). As shown best in FIGS. 4A-5, each of the side portions (46) of the first device half (22) includes a side concave portion (54) positioned centrally between a pair of side planar portions (56) that join at their outer ends with the concave end portions (48). Additionally, each of the side portions (50) of the second device half (24) includes a side convex portion (58) positioned centrally between a pair of side planar portions (60) that join at their outer ends with the convex end portions (52).

Figure 9A:
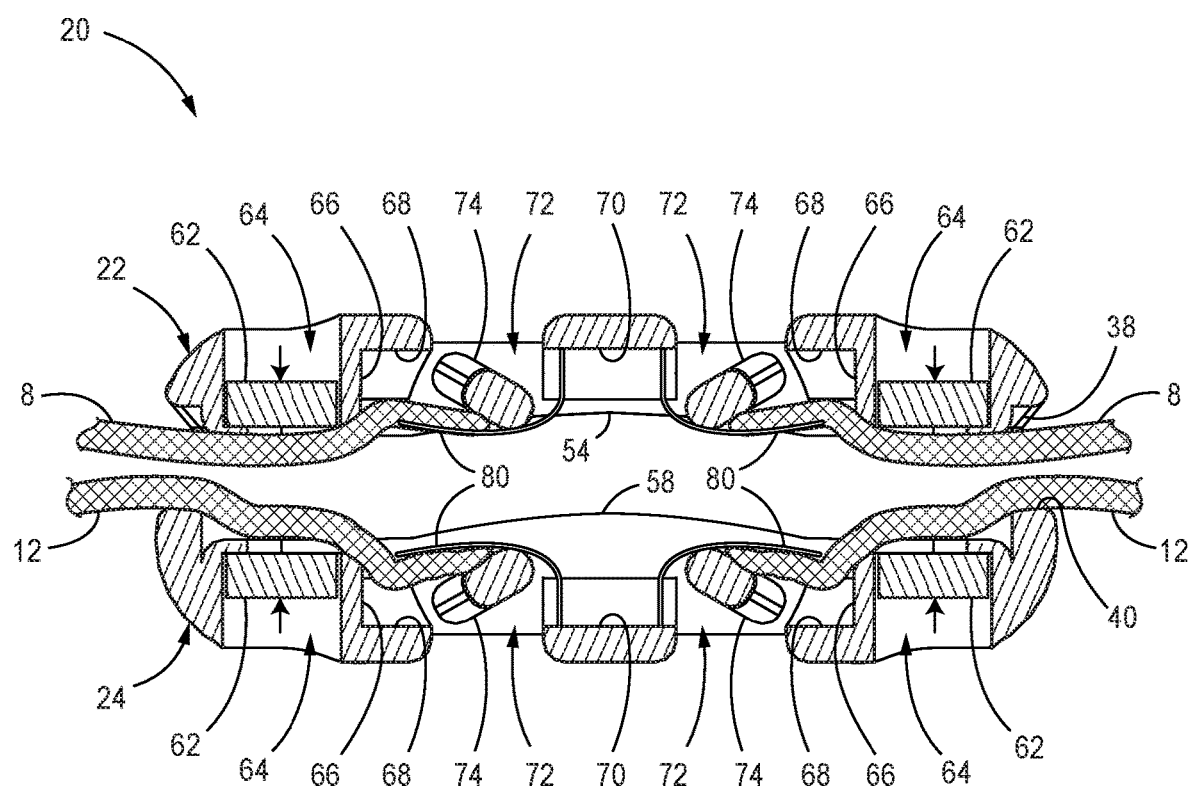
FIG. 9A depicts a side cross-sectional view of the tissue compression device of FIG. 3 following deployment within first and second portions of a patient's small intestine, showing the first and second device halves magnetically drawing together to compress tissue therebetween.
Figure 9B:
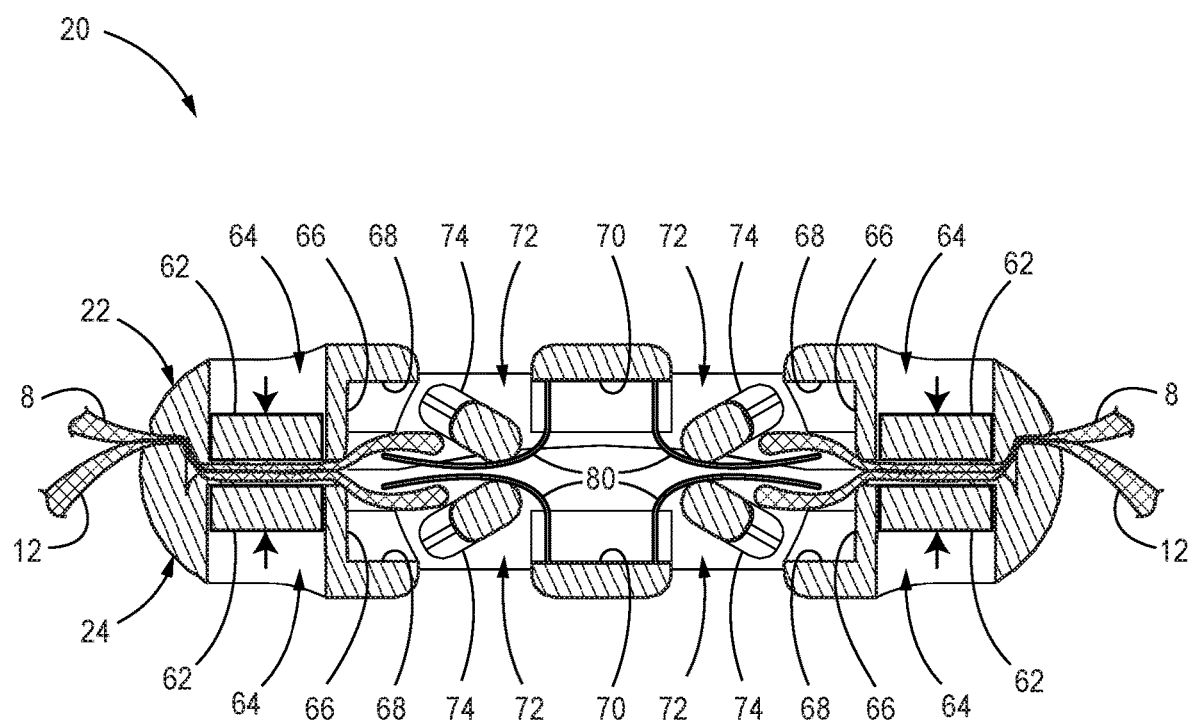
FIG. 9B depicts a side cross-sectional view of the tissue compression device of FIG. 3 in the first and second portions of the patient's small intestine of FIG. 9A, showing further compression of the tissue between the device halves and resulting necrosis of the compressed tissue.
Figure 9C:
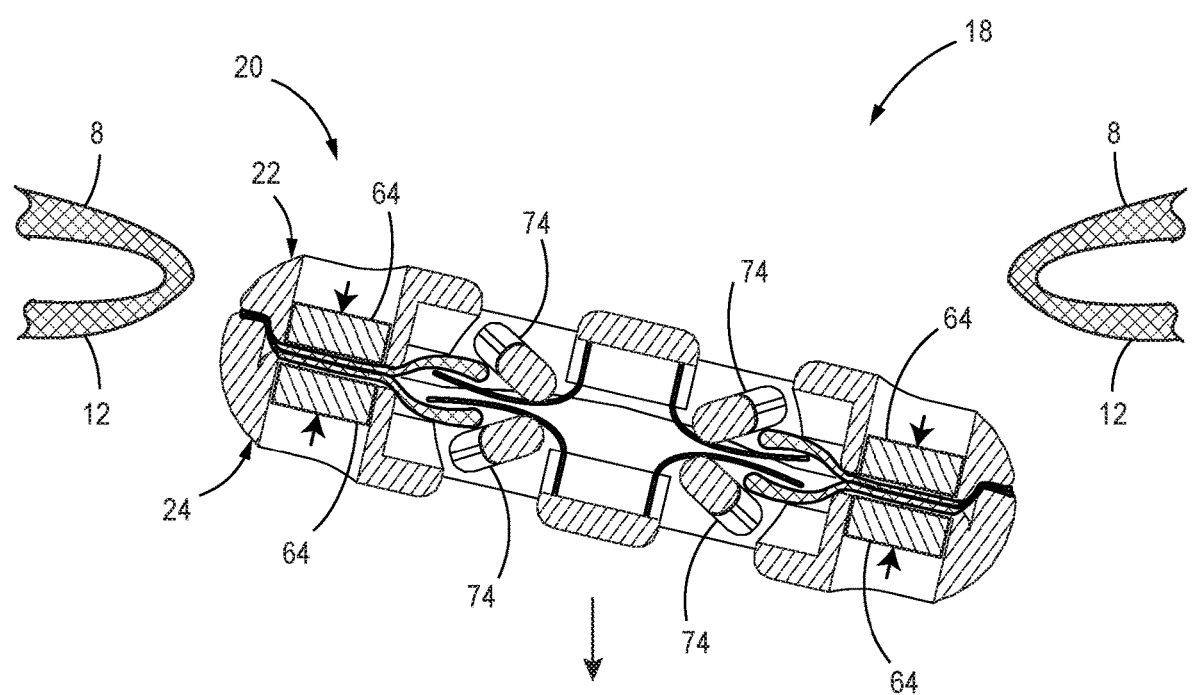
FIG. 9C depicts a side cross-sectional view of the tissue compression device of FIG. 3 in the first and second portions of the patient's small intestine of FIGS. 9A and 9B, showing the compressed tissue in a fully necrosed state, and the device falling away to reveal an anastomosis between the two portions of the small intestine.

As shown best in FIGS. 4A and 4B, the contours of the side concave portions (54) and the side convex portions (58) complement each other. Similarly, the contours of the concave end portions (52) and the convex end portions (52) complement each other. In that regard, portions of the first mating surface (38) are concavely contoured in a direction away from the second mating surface (40), while portions of the second mating surface (40) are convexly contoured in a direction toward the first mating surface (38). This exemplary arrangement of complementary contours facilitates proper alignment of the first and second device halves (22, 24) with one another when clamping together as shown in FIGS. 9A-9C, described below.

As seen by a comparison of FIGS. 4A and 4B, each of the side concave portions (54) and the side convex portions (58) of the first and second mating surfaces (38, 40) may be formed with a first radius of curvature, and each of the concave end portions (48) and convex end portions (52) may be formed with a differing second radius of curvature. As shown, the second radius of curvature may be smaller than the first radius of curvature. Additionally, because the side concave portions (54) and side convex portions (58) each extend generally parallel to the device axis (i.e., along a length of the device (20)), and the concave end portions (48) and convex end portions (52) each extend generally transverse to the device axis (i.e., along a width of the device (20)), the first and second radii of curvature are defined within respective first and second planes that are orthogonal to one another. In particular, the first radius of curvature associated with the side contoured portions (54, 58) is defined within a first plane that extends parallel to the device axis. By comparison, the second radius of curvature associated with the end portions (48, 52) is defined within a second plane that extends orthogonally to the device axis, and orthogonally to the first plane.

As described above, the first mating surface (38) includes concave contours and the second mating surface (40) includes complementary convex contours. In alternative versions, the mating surfaces (38, 40) may be provided with various other arrangements of concave and convex contours suitable to facilitate alignment of the first and second device halves (22, 24) with one another during use, while maintaining adequate compression of tissue positioned therebetween. For example, the first mating surface (38) may include one or more concave portions and/or one or more convex portions, and the second mating surface (40) may include a complementary arrangement of one or more convex portions and/or one or more concave portions. The concave portions and/or convex portions may be separated by one or more planar portions as desired. Further, a first set of one or more mating pairs of the contoured portions may be shaped with a first radius of curvature, while a second set of one or more mating pairs of the contoured portions may be shaped with a second radius of curvature. As described above, the first and second radii of curvature may be defined within respective first and second planes that are orthogonal to one another.

Still referring to FIG. 5, the first device half (22) houses a first pair of magnetic members (62), and the second device half (24) houses a second pair of magnetic members (62). Each magnetic member (62) is received within a respective socket (64) of a respective magnet retaining structure (66) arranged at a respective end of the corresponding device half (22, 24). Each socket (64) extends generally transversely toward the device axis, and opens at a first end to the rounded outer periphery (32, 36) of the respective device half (22, 24), and opens at a second end to the mating side of the device half (22, 24). Each device half (22, 24) includes a pair of recessed end base walls (68) from which the magnet retaining structures (66) project in a direction generally transversely toward the device axis.

Each magnetic member (62) is generally disc-like or cylindrical in shape in the present example, and is fixed at an inner end of its respective socket (64), such as by bond or press fit, for example. Alternatively, the magnetic members (62) may be threadedly engaged with their sockets (64), or one or more of the magnetic members (62) may be slidable within its socket (64) and provided with a latching feature. Such latching feature may be configured to lockingly engage an opposing magnetic member (62) of the other device half (22, 24), for example as disclosed in U.S. patent application Ser. No. 15/419,086, entitled "Magnetic Tissue Compression Device with Backup Mechanical Latch," filed on Jan. 30, 2017, issued as U.S. Pat. No. 10,206,682 on Feb. 19, 2019, the disclosure of which is hereby incorporated by reference herein.

In the present example, each magnetic member (62) is in the form of, or otherwise include, a permanent magnet provided with a magnetic polarity opposite that of the opposing magnetic member (62) carried by the other device half (22, 24). In some versions, the magnetic members (62) of each device half (22, 24) may be provided with opposite polarities. In other embodiments, the magnetic members (62) of the first device half (22) may have a first polarity, while the magnetic members (62) of the second device half (24) may an opposite second polarity. In either case, the magnetic members (62) of each device half (22, 24) are configured to magnetically attract the magnetic members (62) of the other device half (22, 24). Accordingly, the device halves (22, 24) are configured to magnetically draw together and compress tissue positioned therebetween to form an anastomosis, as described in greater detail below.

While the magnetic members (62) are shown in the form of permanent magnets, in alternative versions they may be in the form of electromagnets, for example. In other versions, the magnetic members (62) may include a combination of one or more permanent magnets and one or more electromagnets. In that regard, the tissue compression device (20) may further include a circuit assembly having one or more electromagnets and/or one or more illumination devices or other suitable electrical elements, for example as generally disclosed in U.S. patent application Ser. No. 15/419,102, entitled "Battery Powered Electromagnetic Tissue Compression Device," filed on Jan. 30, 2017, published as U.S. Pub. No. 2018/0214151 on Aug. 2, 2018, the disclosure of which is hereby incorporated by reference herein.

Figure 6:
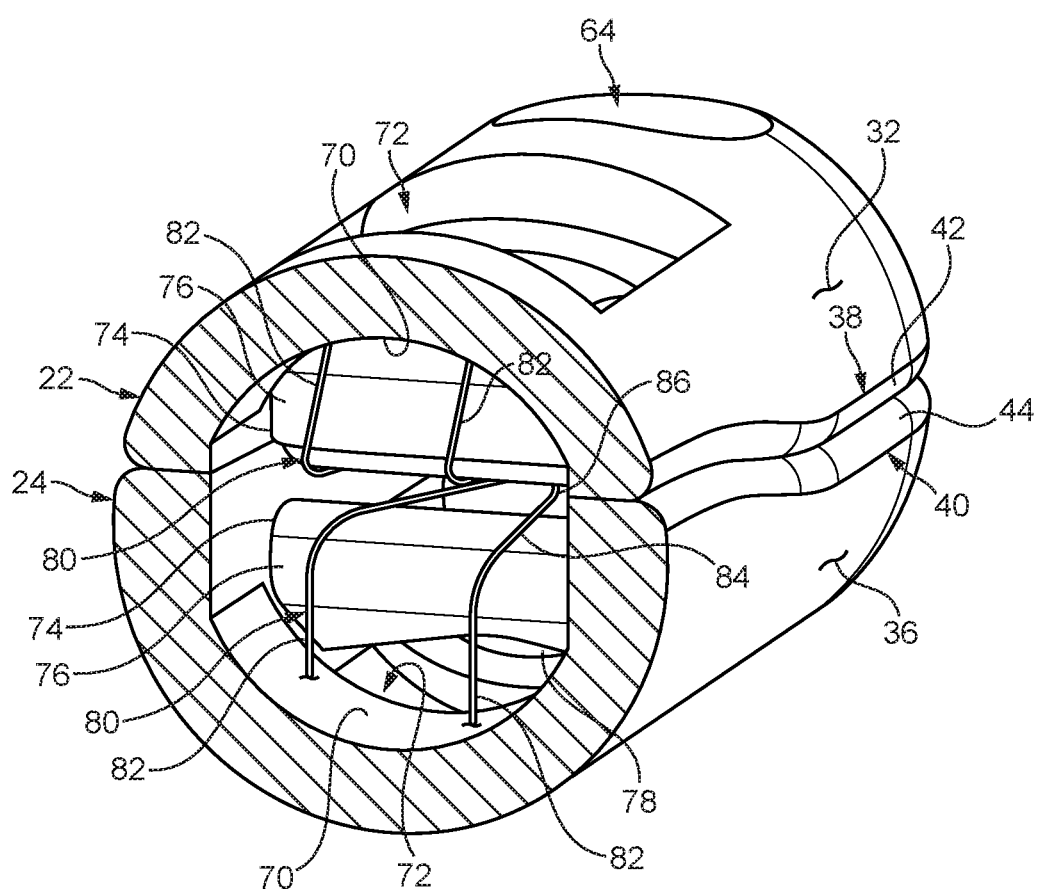
FIG. 6 depicts a transverse cross-sectional view of the tissue compression device of FIG. 3, taken along section line 6-6 of FIG. 3, showing internal features of the device.

Referring to FIGS. 5 and 6, each device half (22, 24) further includes a recessed medial base wall (70) which, along with the recessed end base walls (68), is inwardly recessed from the respective mating surface (38, 40). The medial base wall (70) is positioned between the end base walls (68), and is equally spaced therefrom by a pair of openings (72) formed in the outer periphery (32, 36) of the device half (22, 24), seen also in FIGS. 3 and 7A. In alternative versions, the openings (72) may be omitted from the device halves (22, 24), and the medial base walls (70) may be formed integrally with the end base walls (68) to define a single recessed base wall for each device half (22, 24). In either case, the device halves (22, 24) combine to define an interior cavity bounded by the base walls (68, 70) and the magnet retaining structures (66), as shown in FIG. 9B.

Figure 7A:
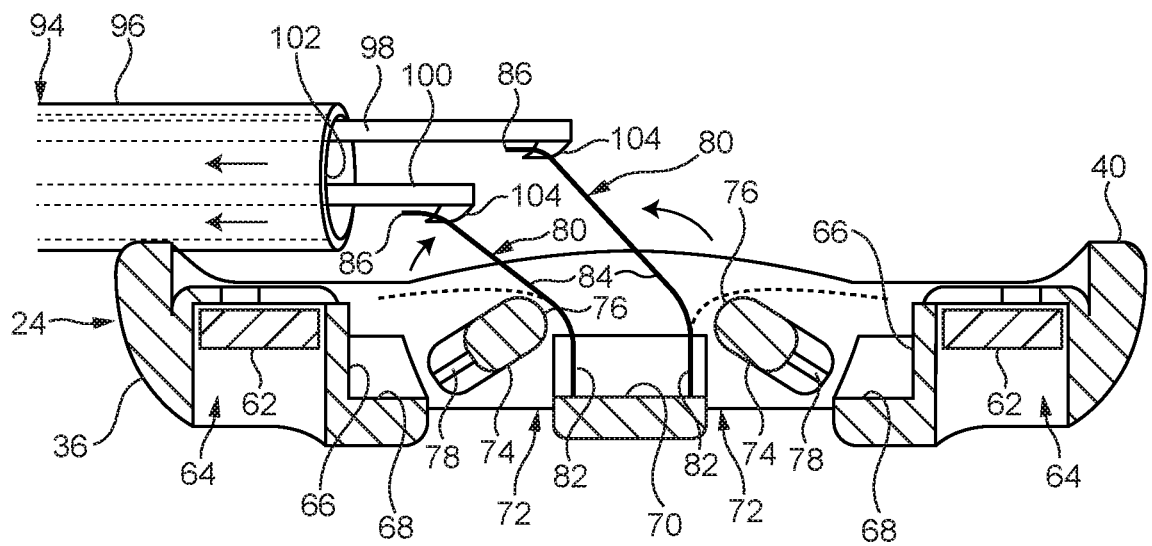
FIG. 7A depicts a side cross-sectional view of a second device half of the tissue compression device of FIG. 3, shown with retaining clips thereof engaged with the distal end of an exemplary instrument operable to deploy the device halves within a patient, with inner members of the instrument shown in extended positions.

Each device half (22, 24) of the present example further includes a pair of bridges (74) extending transversely between the side portions (46, 50) of its mating surface (38, 40). As shown in FIGS. 6 and 7A, each bridge (74) is aligned with a respective one of the openings (72), and spaced therefrom in a direction toward the device axis. Each bridge (74) generally includes a leading edge (76) and a notched trailing edge (78), defined by a generally triangular shaped notch feature having an apex oriented toward the leading edge (76). Each of the leading and trailing edges (76, 78) are rounded in the present example. As shown in FIG. 5, the pair of bridges (74) of each device half (22, 24) are oriented such that the leading edges (76) face one another. Additionally, each bridge (74) is angled relative to the mating surface (38, 40) of its respective device half (22, 24) such that its leading edge (76) is oriented toward the mating surface (38, 40) and its notched trailing edge (78) is oriented toward the adjacent end base wall (68). As described below, the bridges (74) may serve as gripping structures, to be gripped by grasping instruments used to position the device halves (22, 24) within a patient during an anastomosis procedure.

Still referring to FIGS. 5 and 6, each device half (22, 24) further includes a pair of resilient retaining clips (80) in the present example. Each retaining clip (80) includes a pair of legs (82) that couple to and project from the respective recessed medial base wall (70) in a direction toward the device axis, and a body (84) that bends away from the legs (82) in a direction generally parallel to the device axis. The body (84) includes a looped tip (86) oriented toward a respective magnet retaining structure (66). As best shown in FIG. 6, each clip (80) is positioned such that its legs (82) rise toward the leading edge of a respective bridge (74), and its body (84) overlies the bridge (74) with a gap defined therebetween by the tilted orientation of the bridge (74). The retaining clips (80) may be formed of any suitable resilient material, such as nitinol for example, and may include additional features and functionality of resilient members (130) disclosed in U.S. patent application Ser. No. 15/298,816, incorporated by reference above. In some versions, retaining clips (80) comprise a ferrous material. In some such versions, retaining clips (80) experience some degree of magnetic attraction from magnetic members (62). In some other versions, retaining claims are completely non-ferrous, such that magnetic members (62) do not magnetically attract retaining clips (80). In the present example, each clip (80) is resiliently flexible at bends between its legs (82) and its body (84) for flexing between a relaxed state, shown in FIGS. 5 and 6, and one or more flexed states, shown in FIGS. 7A and 7B. As described below, the retaining clips (80) are operable to retain the respective device half (22, 24) in place within an enterotomy formed in a sidewall of an organ during an anastomosis procedure.

The tissue compression device (20) may further include various additional features not shown herein, such as one or more mechanical latching mechanisms, compressible members, and/or suture bores as disclosed in U.S. patent application Ser. No. 15/419,086, issued as U.S. Pat. No. 10,206,682 on Feb. 19, 2019, incorporated by reference above. Such suture bores may be used in combination with suture materials and methods as generally disclosed in U.S. patent application Ser. No. 15/419,151, published as U.S. Pub. No. 2018/0214152 on Aug. 2, 2018, entitled "Tissue Compression Device with Features to Contain Needles and Suture During Packaging and Placement in Body," filed on even date herewith, the disclosure of which is hereby incorporated by reference herein.

B. Exemplary Procedures for Forming an Anastomosis Using Exemplary Tissue Compression Device Having Contoured Mating Surfaces Referring to FIGS. 7A-7F, an exemplary procedure will now be described for deploying the device halves (22, 24) of the tissue compression device (20) within the small intestine (5) of a patient at the site of an anastomosis to be formed. As described below in connection with FIGS. 7C-7E, the first device half (22) is deployed through a first enterotomy (90) into the duodenum (8), and the second device half (24) is deployed through a second enterotomy (92) into an adjacent portion of the ileum (12). The enterotomies (90, 92) may be formed using any suitable cutting instrument known in the art. While specific reference is made to the duodenum (8) and the ileum (12), it will be understood that the device halves (22, 24) may be deployed at various other locations within the gastrointestinal tract (2), or within other organs, at which an anastomosis is to be formed. Further, while the steps illustrated in FIGS. 7A-7D are shown in connection with deploying the second device half (24), it will be understood that similar steps may be taken to deploy the first device half (22).

Figure 7B:
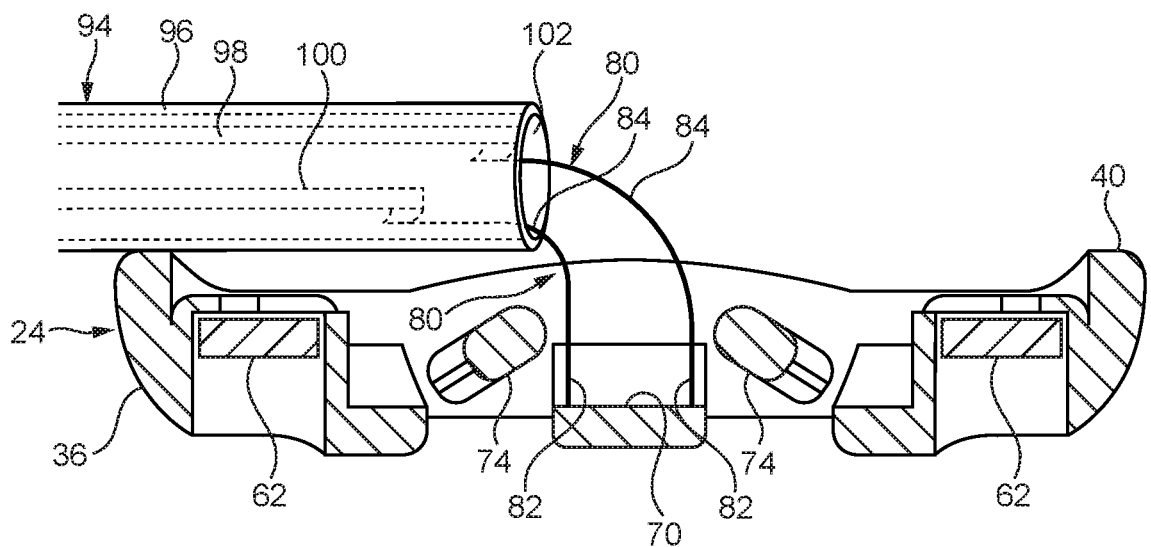
FIG. 7B depicts a side cross-sectional view of the second device half and instrument of FIG. 7A, showing the inner members of the instrument in retracted positions.

An exemplary instrument (94) is used to facilitate deployment of the device halves (22, 24) within a patient. As shown in FIGS. 7A and 7B, the instrument (94) of the present example includes an outer sheath (96) and first and second elongate inner members (98, 100) housed within the outer sheath (96) and spaced radially from one another. A distal end of the outer sheath (96) includes an opening (102) through which distal ends of the inner members (98, 100) slidably extend and retract. The inner members (98, 100) are slidably disposed within the outer sheath (96), and each inner member (98, 100) is translatable between an extended position, shown in FIG. 7A, and a retracted position, shown in FIG. 7B. The distal end of each inner member (98, 100) includes a hook element (104) configured to engage and releasably retain the looped tip (86) of a retaining clip (80). The hook element (104) may be rounded at a leading edge so as to minimize undesirable trauma to patient tissue during a device placement procedure.

To load the device half (24) onto the instrument (94), as shown in FIG. 7A, the inner members (98, 100) are first extended. The hook element (104) of the first inner member (98) is engaged with the looped tip (86) of a first one of the retaining clips (80), and the hook element (104) of the second inner member (100) is engaged with the looped tip (86) of a second one of the retaining clips (80). As shown in FIG. 7A, the hook element (104) of the first inner member (98) is extended distally beyond the hook element (104) of the second inner member (100) to reach its respective retaining clip (80). Once the looped tips (86) have been retained on the hook elements (104), the inner members (98, 100) are retracted into the outer sheath (92), through the distal opening (102). The retaining clips (80) are configured to resiliently flex between relaxed and flexed positions when being engaged by the instrument (94), as shown in FIGS. 7A and 7B.

Figure 7C:
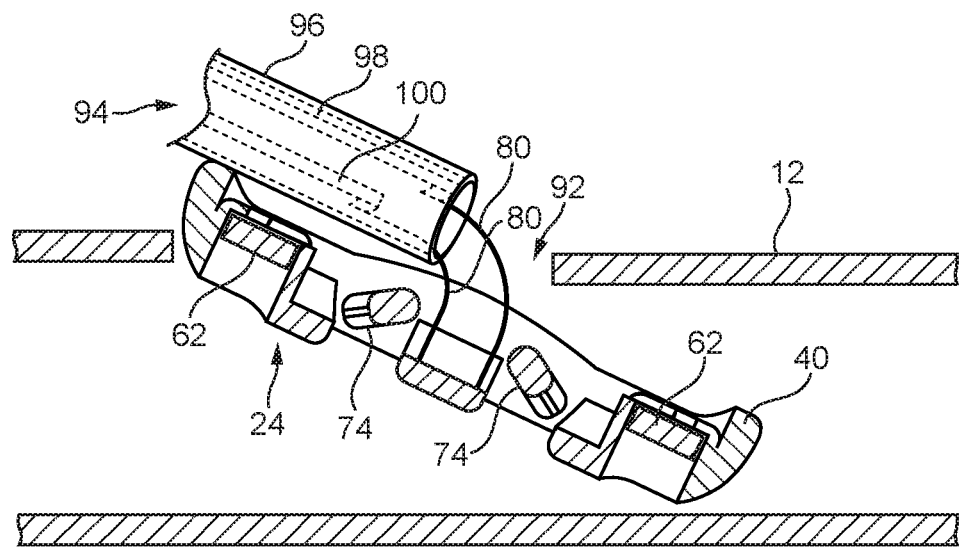
FIG. 7C depicts a side cross-sectional view of a patient's digestive system during deployment of the tissue compression device of FIG. 3 for an anastomosis procedure, showing insertion of the second device half through an enterotomy formed in the patient's ileum, using the instrument of FIG. 7A.
Figure 7D:
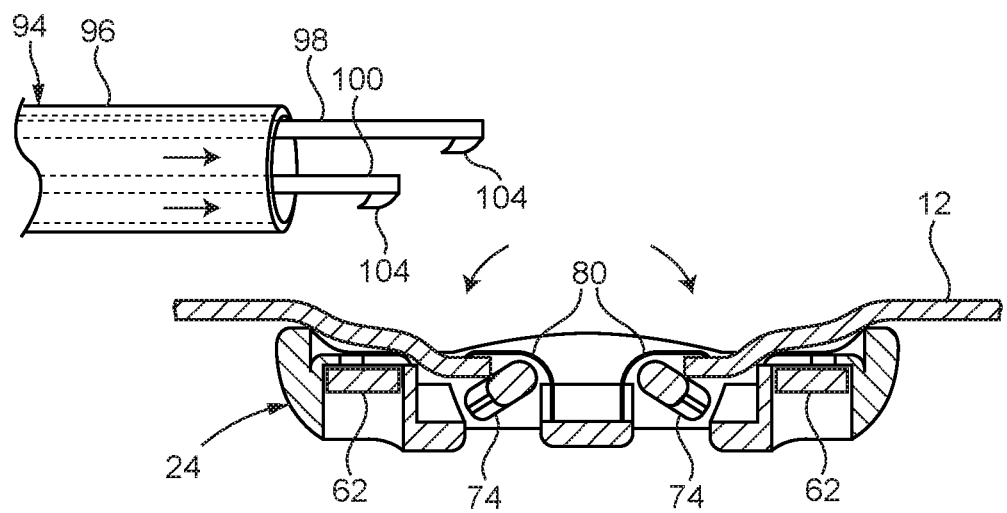
FIG. 7D depicts a side cross-sectional view of the patient's digestive system of FIG. 7C, later during deployment of the tissue compression device of FIG. 3 for an anastomosis procedure, showing the inner members of the instrument moved to their extended positions to release the retaining clips of the second device half into a deployed state for engaging the ileum sidewall.

As shown in FIG. 7C, the loaded device half (24) is inserted by the instrument (94) through the enterotomy (92) formed in the sidewall of the ileum (12). Alternatively, device half (24) may be inserted in any other suitable portion of the patient's gastrointestinal tract (2). Though not shown, a proximal end of the instrument (94) is manipulated by a surgeon to properly locate the device half (24) within the enterotomy (92). As shown in FIG. 7D, once the device half (24) has been suitably positioned within the enterotomy (92), the inner members (98, 100) of the instrument (94) are translated through the distal opening (102) into their extended positions so the hook elements (104) disengage the looped tips (86) of the retaining clips (80). Consequently, the retaining clips (80) spring back toward their relaxed states and capture the tissue sidewall (12) against the bridges (74). In this manner, the device half (24) is held securely in place relative to the enterotomy (92), and the instrument (94) may be removed from the patient. The same process may be implemented for deploying the first device half (22) within the patient, through the first enterotomy (90) formed in the patient's duodenum (8). Alternatively, device half (22) may be inserted in any other suitable portion of the patient's gastrointestinal tract (2).

In alternative versions, rather than using instrument (94) as described above, each device half (22, 24) may be deployed by grasping its bridges (74) with any suitable grasping instrument (not shown). For example, the grasping instrument may be manipulated to grasp the notched trailing edges (78) of the bridges (74) of a particular device half (22, 24), and further manipulated to suitably position the device half (22, 24) within an enterotomy (90, 92) such that the resilient clips (80) engage the surrounding tissue. Advantageously, the openings (72) formed in the outer periphery (32, 36) of each device half (22, 24) may enable grasping elements of the grasping instrument to project through the device half (22, 24), from the open mating side, to thereby achieve a secure grip of the bridges (74) and maximize manipulation control of the device half (22, 24) during placement. The openings (72) may also serve to provide access to the bridges (74) through the outer peripheries (32, 66) of the device halves (22, 24). Accordingly, the openings (72) enable engagement of the bridges (74) with a grasping instrument after the device halves (22, 24) have magnetically coupled together (see FIGS. 7F and 9B), such as during a "bail-out" procedure in which a medical professional wishes to separate the deployed device halves (22, 24) before an anastomosis is formed.

Figure 7E:
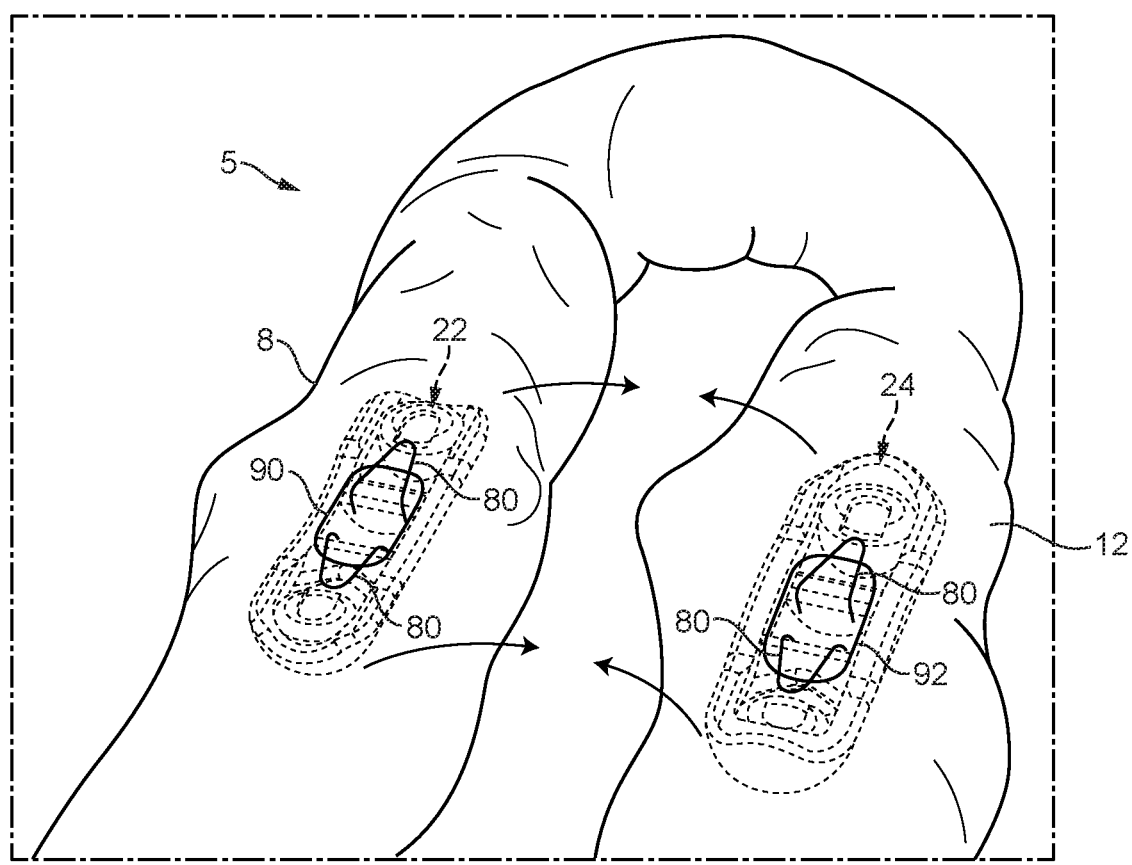
FIG. 7E depicts a perspective view of the small intestine after deployment of the first and second device halves into respective adjacent portions of the small intestine using the exemplary procedure of FIGS. 7A-7D.

FIG. 7E shows the first device half (22) positioned and centered within the first enterotomy (90) formed in the patient's duodenum (8), and the second device half (24) positioned and centered within the second enterotomy (92) formed in an adjacent portion of the patient's ileum (12). The instrument (94) has been removed from the patient and the retaining clips (80) maintain the device halves (22, 24) in position. As indicated by the directional arrows in FIG. 7E, the adjacent portions of the duodenum (8) and the ileum (12), in which the device halves (22, 24) have been deployed, may be repositioned as necessary to arrange the first and second enterotomies (90, 92), and the device halves (22, 24) arranged therein, in confronting relation.

Figure 7F:
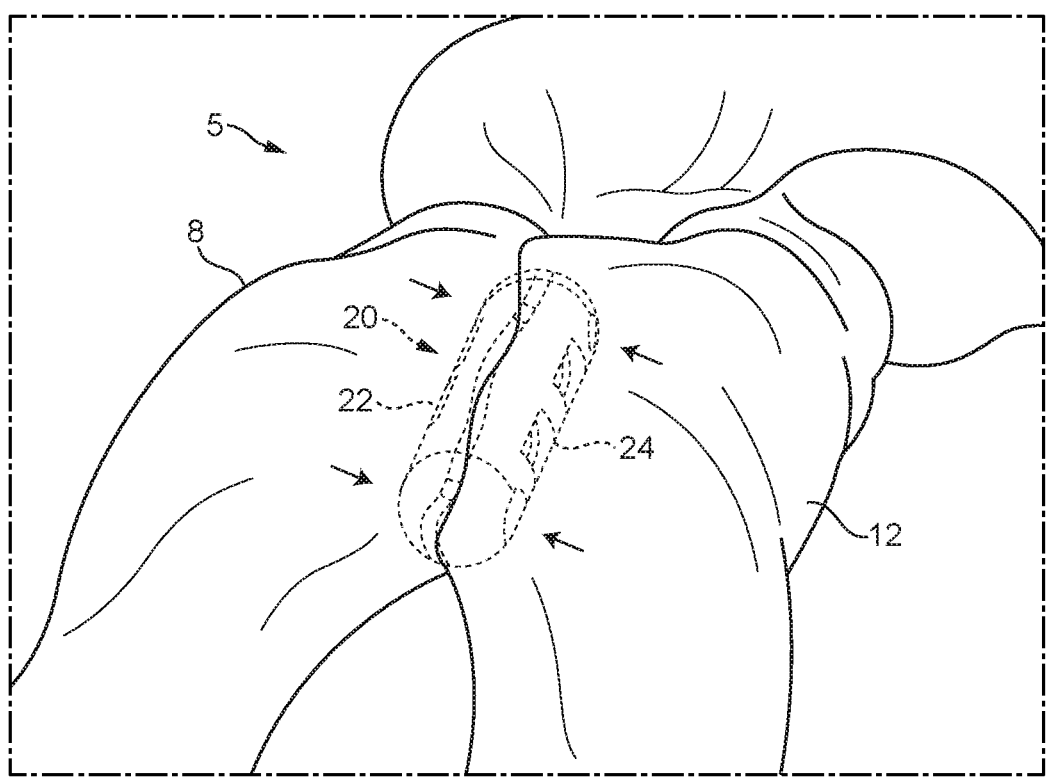
FIG. 7F depicts a perspective view similar to FIG. 7E, showing the first and second device halves magnetically drawing together to compress intestinal tissue therebetween for forming an anastomosis.

As shown in FIG. 7F, once the mating sides of the device halves (22, 24) are brought within proximal range of each another, the magnetic members (62) of the device halves (22, 24) mutually attract one another and draw the two device halves (22, 24) together. As described in greater detail below in connection with FIGS. 9A-9C, the device halves (22, 24) thereby compress the sidewalls of the duodenum (8) and the ileum (12) between their mating surfaces (38, 40), and cause the formation of an anastomosis.

Figure 8A:
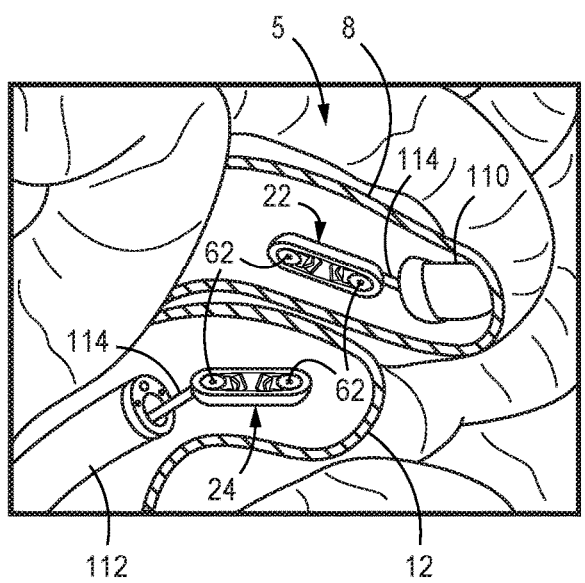
FIG. 8A depicts a cutaway perspective view of the patient's small intestine, showing another exemplary procedure for deploying the tissue compression device of FIG. 3 within the small intestine, using endoscopes.
Figure 8B:
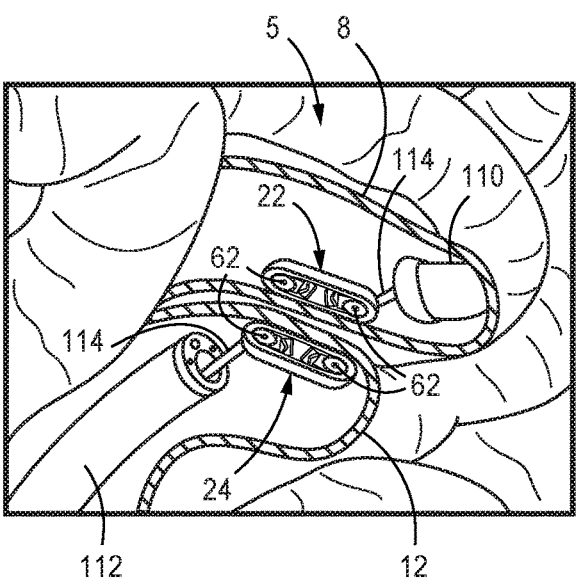
FIG. 8B depicts a cutaway perspective view of the procedure of FIG. 8A, showing the first and second device halves being aligned with one another within their respective adjacent portions of the small intestine, using the endoscopes.
Figure 8C:
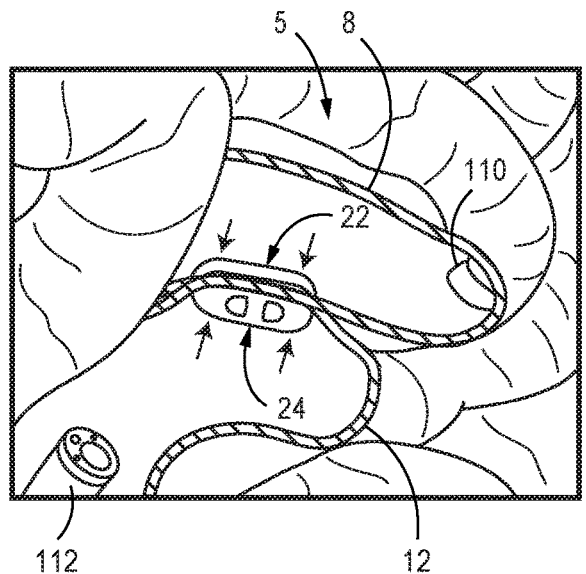
FIG. 8C depicts a cutaway perspective view of the procedure of FIG. 8A, showing the first and second device halves disengaged from the endoscopes and magnetically drawing together to compress the small intestine sidewalls therebetween for forming an anastomosis.

As described above, the exemplary device deployment procedure shown in FIGS. 7A-7F includes the formation of enterotomies (90, 92) in a patient's gastrointestinal tract (2). In some instances, it may be desirable to avoid formation of such enterotomies. FIGS. 8A-8C show an exemplary alternative device deployment procedure in which the device halves (22, 24) are deployed within the patient's gastrointestinal tract (2) using endoscopes (110, 112), and without forming enterotomies in the tract (2). In this version, the retaining clips (80) are not used and may be omitted from the tissue compression device (20), if desired. While specific reference is made below to the duodenum (8) and the ileum (12), it will be understood that this exemplary procedure may be used for deploying the device halves (22, 24) at various other locations within the gastrointestinal tract (2), or within other organs, at which an anastomosis is to be formed.

Referring to FIG. 8A, the first device half (22) is loaded onto a retractable inner member (114) of the first endoscope (110) and the second device half (24) is loaded onto a retractable inner member (114) of the second endoscope (112). The endoscopes (110, 112) may be of any suitable types known in the art. The first endoscope (110) is then inserted through a first natural body orifice (e.g., mouth) at a first end of the patient's gastrointestinal tract (2), and the second endoscope (112) is inserted through a second natural body orifice (e.g., rectum) located at a second end of the gastrointestinal tract (2). The distal ends of the endoscopes (110, 112), loaded with the device halves (22, 24), are then routed through the gastrointestinal tract (2), from opposing directions, toward a site at which an anastomosis is to be formed.

Referring to FIG. 8B, the exemplary site for anastomosis formation is shown selected at adjacent portions of the patient's duodenum (8) and ileum (12). Upon reaching the anastomosis site, the endoscopes (110, 112) are manipulated to approximately align the device halves (22, 24) so that their mating surfaces (38, 40) (see FIG. 5) confront one another. As shown in FIG. 8C, upon the device halves (22, 24) being approximately aligned, the magnetic members (62) attract one another through the tissue sidewalls (8, 12) and draw the device halves (22, 24) together, thereby compressing the sidewalls (8, 12) between the mating surfaces (38, 40). As shown in FIG. 8C, compression of the sidewalls (8, 12) between the device halves (22, 24) secures the device halves (22, 24) in place relative to each other and relative to the sidewalls (8, 12). The inner members (114) of the endoscopes (110, 112) may then be detached from the device halves (22, 24) and retracted, and the endoscopes (110, 112) may be removed from the patient by reversing them through the gastrointestinal tract (2).

FIGS. 9A-9C show formation of an exemplary anastomosis in sidewalls of the patient's duodenum (8) and ileum (12). The device halves (22, 24) are shown including retaining clips (80), and thus FIGS. 9A-9C may be understood to show the device halves (22, 24) after having been positioned using the exemplary instrument (94) and placement procedure shown in FIGS. 7A-7D. However, as described above, the device halves (22, 24) may alternatively be positioned using the exemplary endoscopic procedure shown in FIGS. 8A-8C, in which case enterotomies are not formed in the intestinal sidewalls (8, 12) and the retaining clips (80) may be omitted from the device halves (22, 24). It will be appreciated that the device engagement steps described below, and the resulting anastomosis formation, may apply regardless of the technique used to initially position the device halves (22, 24) within the patient.

Starting with FIG. 9A, the first device half (22) is shown supported by its retaining clips (80) within the first enterotomy (90) formed in the sidewall of the duodenum (8), and the second device half (24) is shown supported by its retaining clips (80) within the second enterotomy (92) formed in the sidewall of the ileum (12). The duodenum (8) and ileum (12) have been positioned so that the enterotomies (90, 92), and the device halves (22, 24) arranged therein, confront one another. Such positioning brings the magnetic members (62) of the first device half (22) into close enough range with the magnetic members (62) of the second device half (24) that the magnetic members (62) begin to attract one another through the tissue sidewalls (8, 12) and draw the two device halves (22, 24) together.

As shown in FIG. 9B, the magnetic attraction between the magnetic members (62) operates to draw the device halves (22, 24) together and compress the sidewalls of the duodenum (8) and the ileum (12) between the first and second mating surfaces (38, 40). The contoured configuration of the mating surfaces (38, 40), described above, facilitates proper alignment of the device halves (22, 24) with one another as they draw together. Additionally, the rounded outer edges (42, 44) of the mating surfaces (38, 40) (see FIG. 5) minimize friction between the mating surfaces (38, 40) and the tissue sidewalls (8, 12), and thereby help to prevent binding of the tissue sidewalls (8, 12) as the device halves (22, 24) mate together.

Compression of the tissue sidewalls (8, 12) between the mating surfaces (38, 40) induces serosa-to-serosa adhesion between the sidewalls (8, 12) at a perimeter surrounding the device (20). Additionally, the compressive clamping force exerted by the mating surfaces (38, 40) is sufficient to cause ischemia and eventual necrosis in the clamped tissue. With passage of time, such as approximately four days to two weeks, for example, the compressed tissue fully necroses and detaches from the surrounding healthy tissue (8, 12), now bonded together via serosa-to-serosa adhesion. Advantageously, the smooth outer periphery and low-profile, pill-shaped configuration of the device (20) minimizes interference of fluid flow through the duodenum (8) and ileum (12) during the necrosis period.

As shown in FIG. 9C, detachment of the necrosed tissue from the surrounding healthy tissue (8, 12) releases the tissue compression device (20) into the small intestine (5), and reveals a formed anastomosis (18). The device (20) continues on through the large intestine (6) and is eventually passed by the patient. Advantageously, the smooth outer periphery and low-profile, pill-shaped configuration of the device (20) facilitates downstream passage of the device (20) through the gastrointestinal tract (2), including the ileocecal valve (17), for example.

Figure 10:
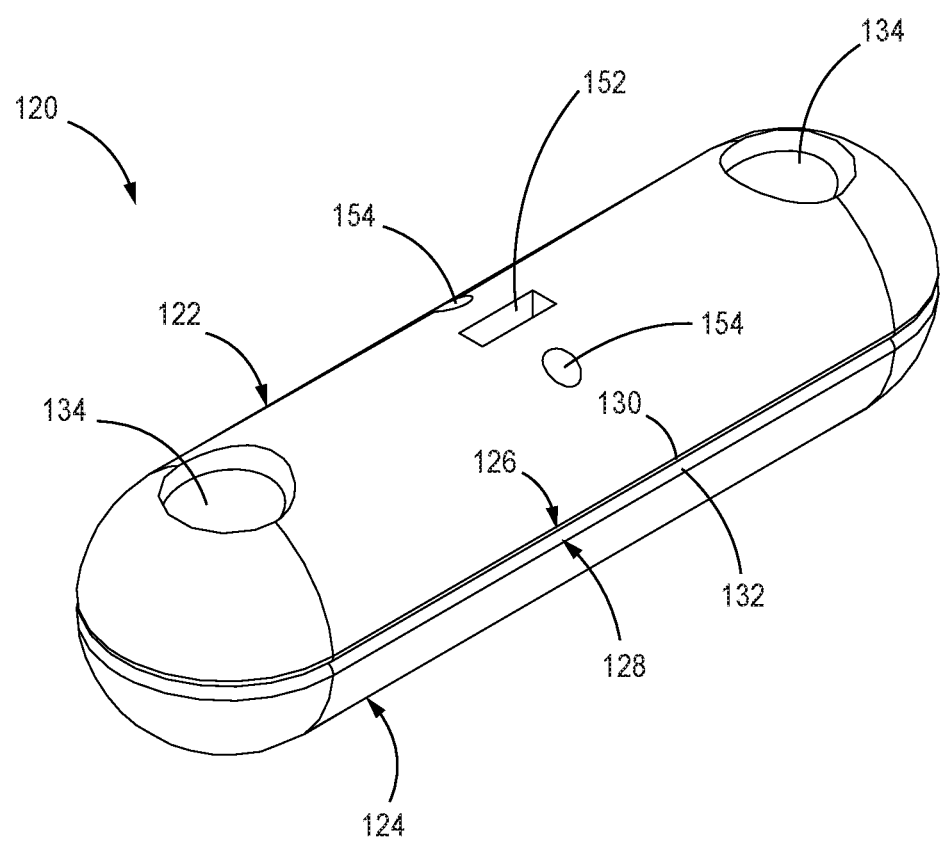
FIG. 10 depicts a perspective view of another exemplary tissue compression device for forming an anastomosis.
Figure 11:
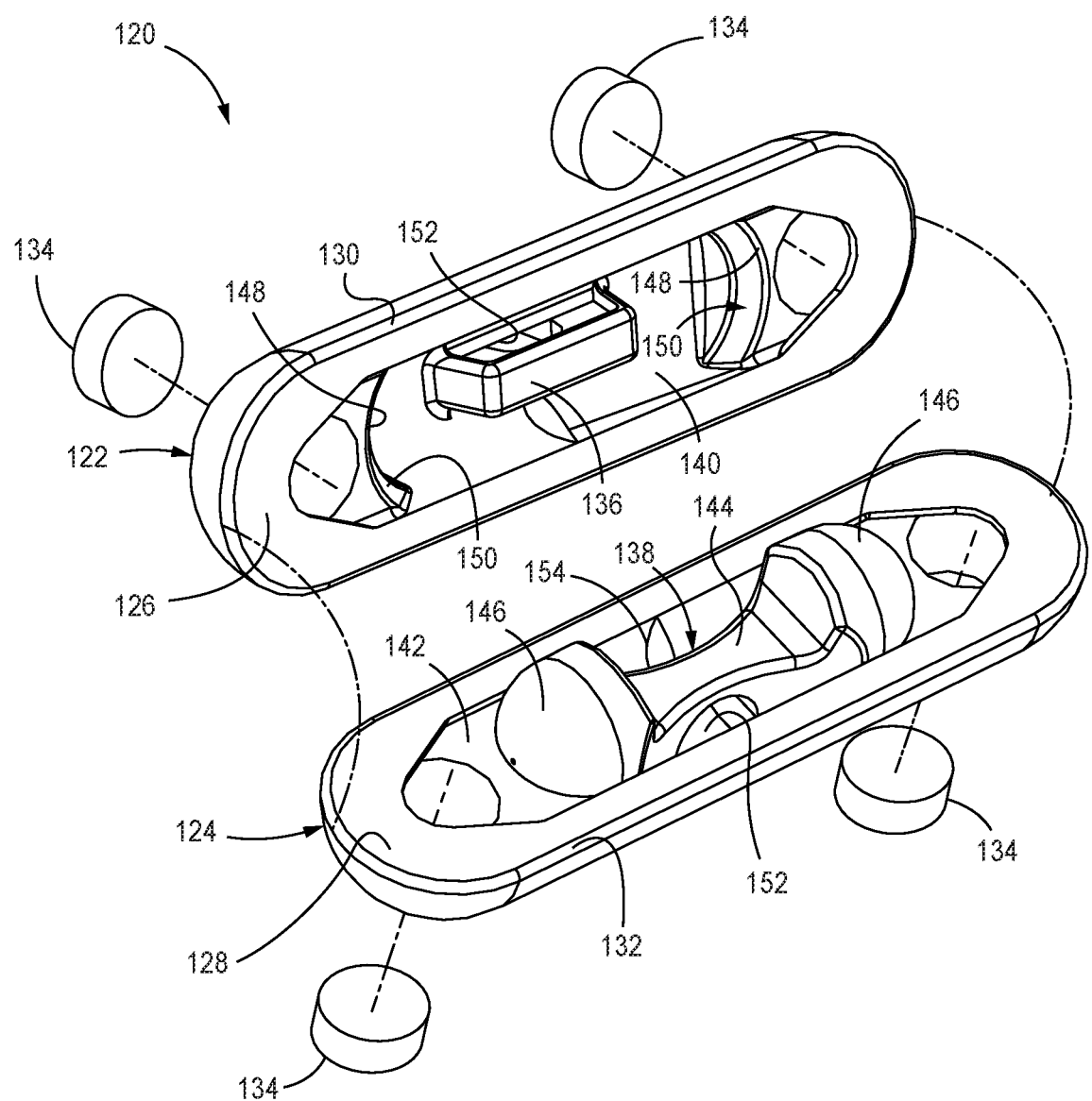
FIG. 11 depicts a disassembled perspective view of the tissue compression device of FIG. 10, showing details of internal compression members supported by the device halves.

C. Exemplary Alternative Anastomosis Tissue Compression Device Having Mating Internal Compression Members FIGS. 10 and 11 show an exemplary alternative tissue compression device (120) for forming an anastomosis, such as a side-by-side anastomosis. The device (120) includes a first device half (122) and a second device half (124) that mate together to define an elongate device body that extends along a longitudinal device axis between convexly rounded first and second ends similar to ends (26, 28) of tissue compression device (20).

Similar to tissue compression device (20) described above, tissue compression device (120) is formed with a length that is greater than its width so as to present an elongate, low-profile, pill-shaped structure. Additionally, device (120) is formed with a transverse cross-section having a rounded shape to provide the device (120) with a rounded and smooth outer periphery. As shown in FIG. 11, the device (120) includes first and second mating surfaces (126, 128), each of which is generally planar and includes a rounded outer edge (130, 132) that transitions smoothly to the smooth outer periphery of the device half (122, 124). In alternative versions, the mating surfaces (126, 128) may be similar in geometric configuration to the first and second mating surfaces (38, 40), respectively, of device (20).

Figure 12A:
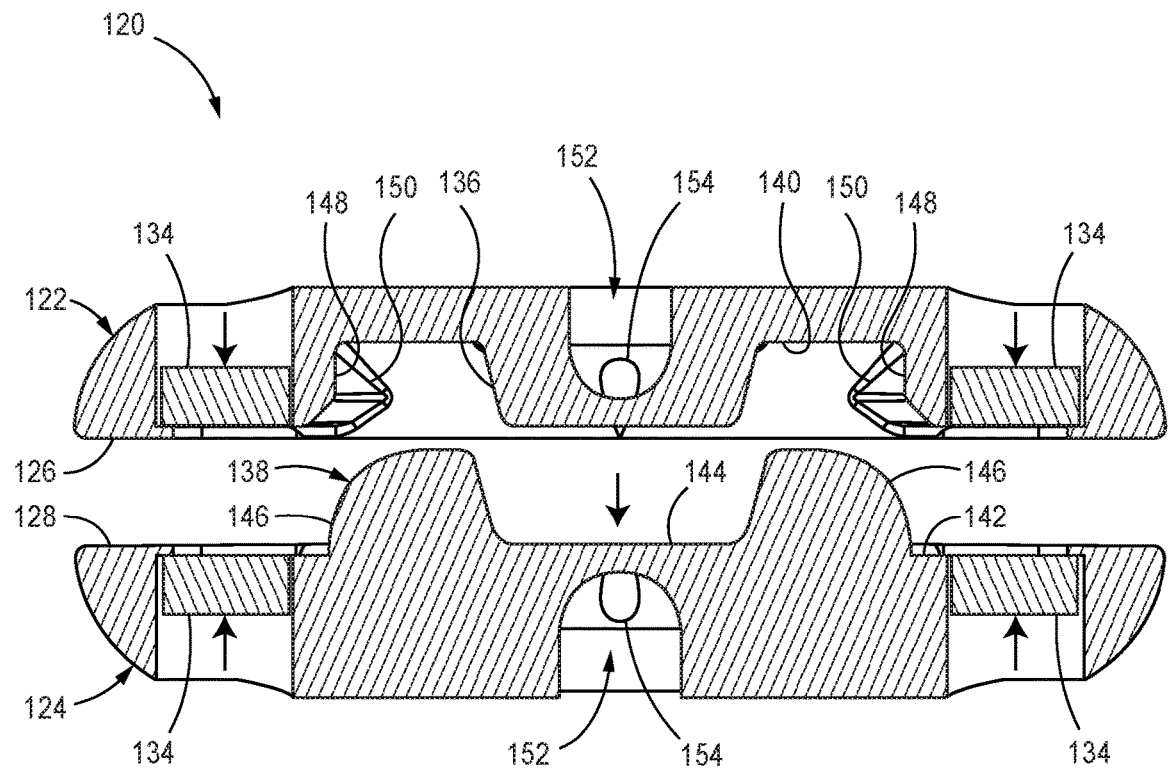
FIG. 12A depicts a side cross-sectional view of the tissue compression device of FIG. 10, showing the device halves magnetically drawing together.
Figure 12B:
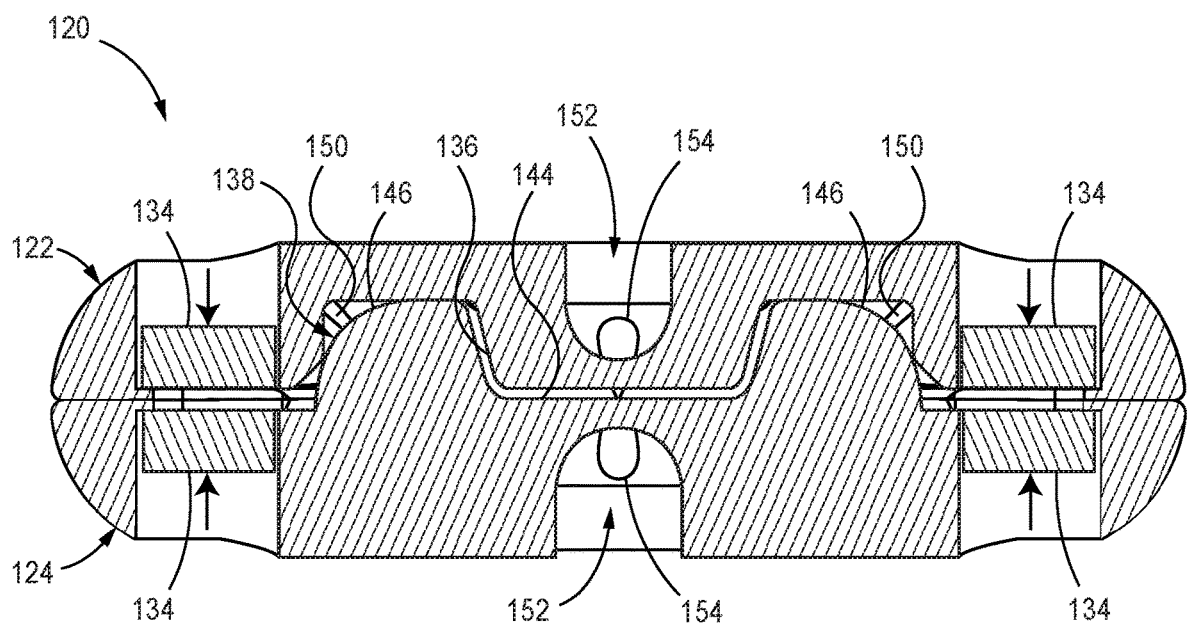
FIG. 12B depicts a side cross-sectional view of the tissue compression device of FIG. 10, showing the device halves magnetically coupled together with the internal compression members mated with one another.

Referring to FIGS. 11-12B, the first device half (122) of tissue compression device (120) houses a first pair of magnetic members (134), and the second device half (124) houses a second pair of magnetic members (134). The magnetic members (134) may be similar in configuration to magnetic members (62) of the tissue compression device (20). As shown in FIGS. 12A and 12B, the magnetic members (134) draw the device halves (122, 124) together magnetically to compress tissue positioned therebetween.

As shown best in FIG. 11, the first device half (122) includes a first internal compression member (136) and the second device half (124) includes a second internal compression member (138) configured to mate with the first internal compression member (136) and compress tissue therebetween. The first internal compression member (136) is shown in the form of an elongate, tab-like structure that projects from a recessed base wall (140) of the first device half (122) and tapers in a direction toward the device axis. The second internal compression member (138) is shown in the form of a dumbbell-shaped structure that projects from a recessed base wall (142) of the second device half (124) in a direction toward the device axis. The second compression member (138) includes a central recess (144) shaped to receive the first compression member (136), and a pair of convex spherical end elements (146). As best shown in FIGS. 11 and 12B, magnet retaining structures (148) formed on the first device half (122) include concave spherical surfaces (150) configured to receive the convex spherical end elements (146) when the device halves (122, 124) are combined. Accordingly, when the first and second device halves (122, 124) are magnetically drawn together during use, tissue is compressed between the internal compression members (136, 138) and simultaneously between the mating surfaces (126, 128).

As shown best in FIGS. 10 and 12A-12B, each device half (122, 124) of the present example further includes an opening (152) that extends through the outer periphery of the device half (122, 124) and into a medial portion of the respective internal compression member (136, 138). Additionally, the tissue compression device (120) includes a pair of suture bores (154) extending transversely through the device halves (122, 124). The suture bores (154) may be employed to suture the device halves (122, 124) in place during an anastomosis procedure, for example as disclosed in U.S. patent application Ser. No. 15/419,151, published as U.S. Pub. No. 2018/0214152 on Aug. 2, 2018, incorporated by reference above. In some other versions, suture bores (154) are omitted.

Figure 13:
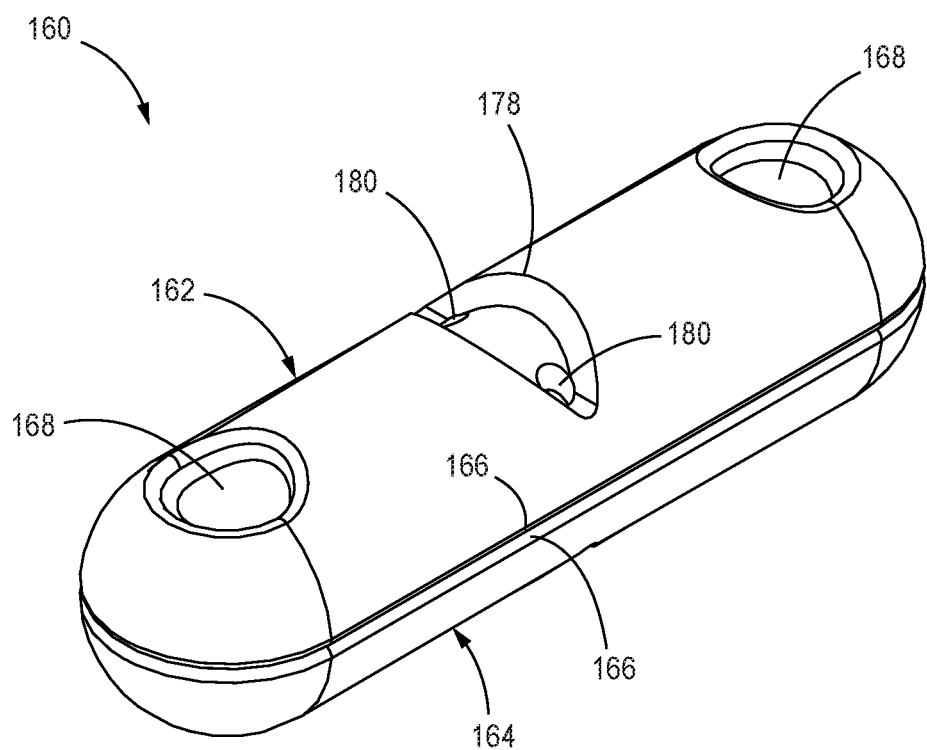
FIG. 13 depicts a perspective view of another exemplary tissue compression device for forming an anastomosis.

D. Exemplary Alternative Anastomosis Tissue Compression Device Having Abutting Internal Compression Members FIG. 13 shows another exemplary alternative tissue compression device (160) for forming an anastomosis, such as a side-by-side anastomosis. The device (160) includes a first device half (162) and a second device half (164) that mate together to define an elongate device body that extends along a longitudinal device axis between convexly rounded first and second ends similar to ends (26, 28) of tissue compression device (20). The device halves (162, 164) are identical in configuration in this example. Each device half (162, 164) includes a mating surface (166) and a pair of magnetic members (168) similar to the mating surfaces (126, 128) and magnetic members (134), respectively, of device (120). In alternative versions, the mating surfaces (166) may be similar in geometric configuration to the first and second mating surfaces (38, 40), respectively, of device (20).

Figure 14:
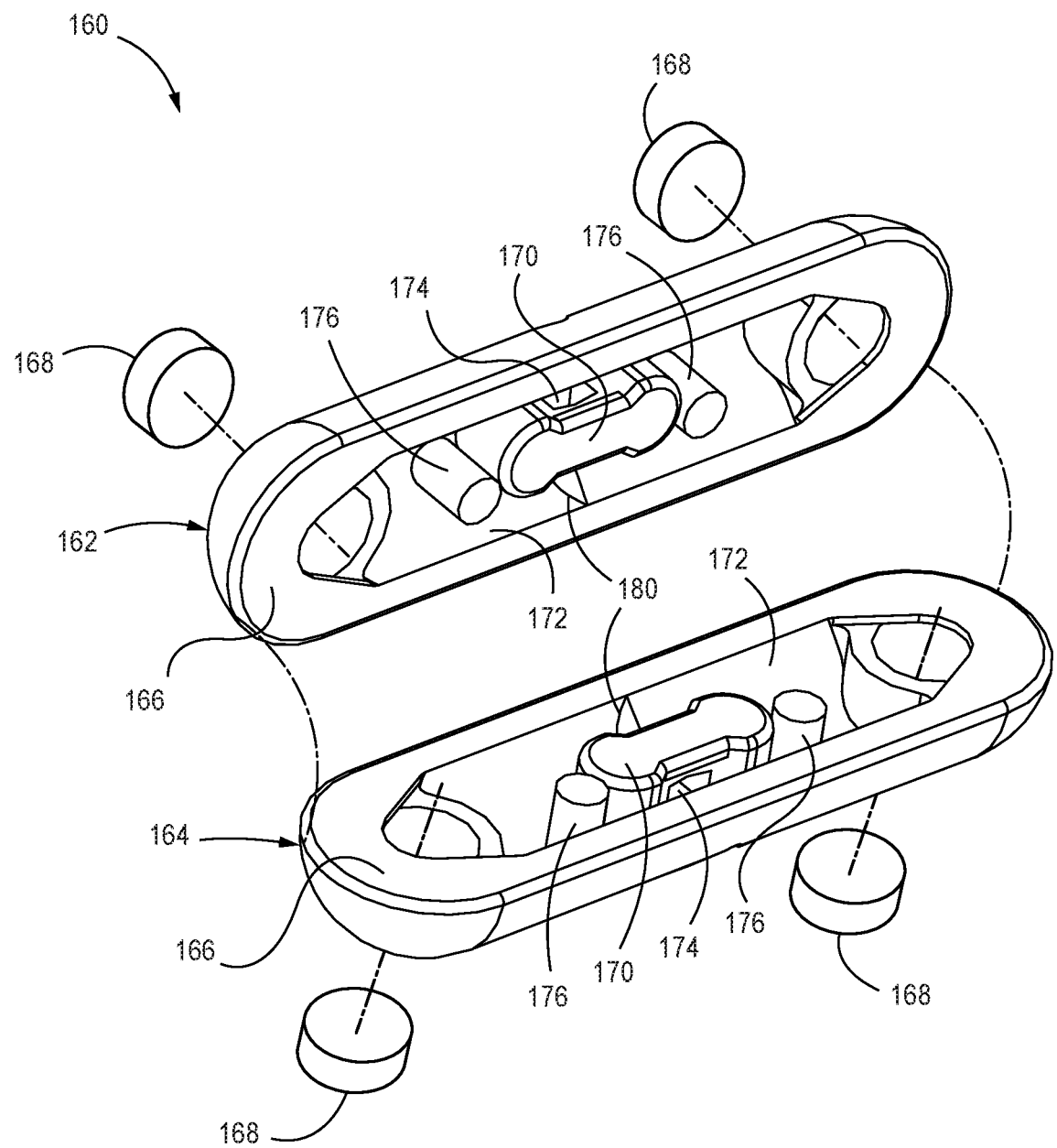
FIG. 14 depicts a disassembled perspective view of the tissue compression device of FIG. 13, showing details of internal compression members supported by the device halves.
Figure 15A:
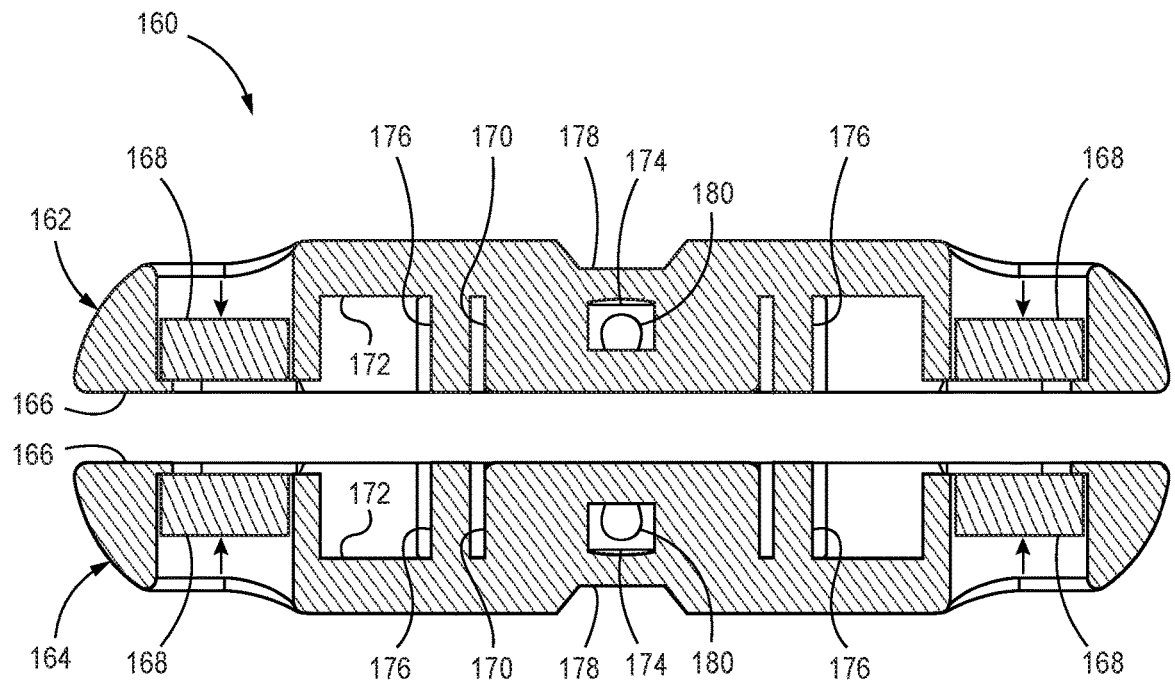
FIG. 15A depicts a side cross-sectional view of the tissue compression device of FIG. 13, showing its first and second device halves magnetically drawing together.
Figure 15B:
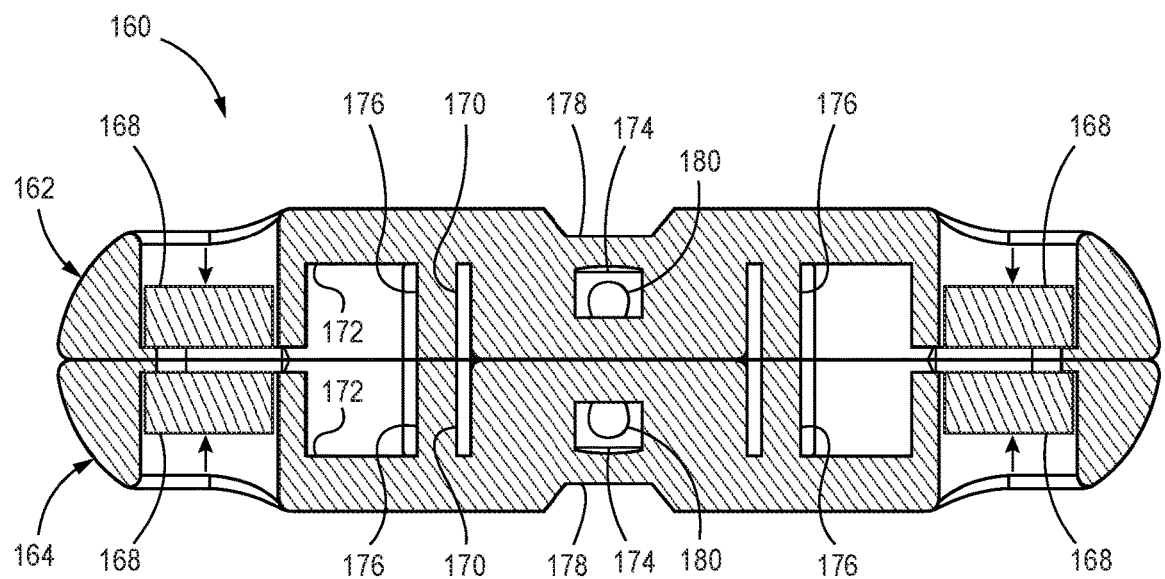
FIG. 15B depicts a side cross-sectional view of the tissue compression device of FIG. 13, showing the device halves magnetically coupled together with the internal compression members abutting one another.

Referring to FIGS. 14-15B, each device half (162, 164) includes a primary internal compression member (170), shown in the form of an extruded dog bone-shaped structure, projecting from a recessed base wall (172) in a direction toward the device axis. A base portion of the primary compression member (170) includes a passage (174) extending transversely therethrough. Each device half (162, 164) further includes a pair of secondary internal compression members (176), shown in the form of cylindrical posts, spaced longitudinally from the ends of the primary compression member (170). As shown in FIGS. 15A and 15B, the primary compression member (170) and the secondary compression members (176) of the first device half (162) are configured to abut the primary compression member (170) and secondary compression members (176), respectively, of the second device half (164) when the device halves (162, 164) mate. Accordingly, as the device halves (162, 164) are drawn together magnetically by the magnetic members (168), tissue is compressed between the internal compression members (170, 176) and simultaneously between the mating surfaces (166).

As best shown in FIGS. 13 and 15A-15B, each device half (162, 164) further includes a wedge-shaped notch (178) extending through its outer periphery and located centrally between the magnetic members (168). Additionally, one or more suture bores (180) extend through the wedge-shaped notch (178) and open to the recessed base surface (172), to enable the device halves (162, 164) to be sutured in place during deployment within a patient, as described above. In some other versions, suture bores (180) are omitted.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue compression device for forming an anastomosis between first and second anatomical structures, the device comprising: (a) a first device portion having a first mating surface; and (b) a second device portion having a second mating surface configured to mate with the first mating surface to compress tissue positioned therebetween, wherein each of the first and second mating surfaces includes a contoured portion, wherein the contoured portions are configured to mate with one another to facilitate alignment of the first and second device portions.

Example 2

The tissue compression device of Example 1, wherein the contoured portion of the first mating surface is shaped with a first contour that complements a second contour of the contoured portion of the second mating surface.

Example 3

The tissue compression device of Example 2, wherein one of the contoured portions is shaped with a concave contour and the other of the contoured portions is shaped with a complementary convex contour.

Example 4

The tissue compression device of any one or more of Examples 1 through 3, wherein each of the first and second mating surfaces includes a first contoured portion shaped with a first radius of curvature and a second contoured portion shaped with a differing second radius of curvature.

Example 5

The tissue compression device of Example 4, wherein the first radius of curvature of the first contoured portion is defined within a first plane and the second radius of curvature of the second contoured portion is defined within a second plane orthogonal to the first plane.

Example 6

The tissue compression device of any one or more of Examples 4 through 5, wherein the first contoured portion extends along a length of the respective device portion and the second contoured portion extends along a width of the respective device portion.

Example 7

The tissue compression device of any one or more of Examples 1 through 6, wherein each of the first and second mating surfaces includes first and second side portions and first and second end portions, wherein the first and second side portions of the first mating surface are configured to mate with the first and second side portions, respectively, of the second mating surface, and the first and second end portions of the first mating surface are configured to mate with the first and second end portions, respectively, of the second mating surface.

Example 8

The tissue compression device of Example 7, wherein the first side portions of the first and second mating surfaces are shaped with complementary contours, and the second side portions of the first and second mating surfaces are shaped with complementary contours.

Example 9

The tissue compression device of Example 8, wherein each of the side portions of the first mating surface is shaped with a concave contour, and each of the side portions of the second mating surface is shaped with a convex contour that complements the concave contour of the corresponding side portion of the first mating surface.

Example 10

The tissue compression device of any one or more of Examples 7 through 9, wherein the first end portions of the first and second mating surfaces are shaped with complementary contours, and the second end portions of the first and second mating surfaces are shaped with complementary contours.

Example 11

The tissue compression device of Example 10, wherein each of the end portions of the first mating surface is shaped with a concave contour, and each of the end portions of the second mating surface is shaped with a convex contour that complements the concave contour of the corresponding end portion of the first mating surface.

Example 12

The tissue compression device of any one or more of Examples 7 through 11, wherein each of the side portions of the first and second mating surfaces is shaped with a first radius of curvature, and each of the end portions of the first and second mating surfaces is shaped with a differing second radius of curvature.

Example 13

The tissue compression device of any one or more of Examples 7 through 12, wherein the first and second side portions of each of the mating surfaces extend in directions parallel to one another.

Example 14

The tissue compression device of any one or more of Examples 1 through 13, wherein each of the first and second mating surfaces includes first and second contoured side portions and first and second contoured end portions.

Example 15

The tissue compression device of any one or more of Examples 1 through 14, wherein each of the side portions and end portions of the first device portion is shaped with a concave contour, and each of the side portions and end portions of the second device portion is shaped with a convex contour.

Example 16

The tissue compression device of any one or more of Examples 1 through 15, wherein each of the device portions includes a body having a unitary structure and formed with a length greater than its width.

Example 17

The tissue compression device of any one or more of Examples 1 through 16, wherein the first and second device portions are configured to magnetically attract one another to compress tissue positioned between the first and second mating surfaces.

Example 18

A tissue compression device for forming an anastomosis between first and second anatomical structures, the device comprising: (a) a first device portion having a first mating surface; and (b) a second device portion having a second mating surface configured to mate with the first mating surface, wherein the first and second device portions are configured to magnetically draw together to compress tissue positioned between the first and second mating surfaces; wherein at least a portion of the first mating surface is concavely contoured in a direction away from the second mating surface, wherein at least a portion of the second mating surface is convexly contoured in a direction toward the first mating surface.

Example 19

The tissue compression device of Example 18, wherein each of the first and second mating surfaces includes first and second contoured side portions and first and second contoured end portions.

Example 20

A tissue compression device for forming an anastomosis between first and second anatomical structures, the device comprising: (a) a first device portion including a unitary body having a first mating surface and a rounded outer periphery extending between first and second side portions of the first mating surface; (b) a second device portion including a unitary body having a second mating surface and a rounded outer periphery extending between first and second side portions of the second mating surface; (c) a first magnetic member supported by the first device portion; and (d) a second magnetic member supported by the second device portion; wherein the first and second magnetic members are configured to draw the first and second device portions together to engage the first and second mating surfaces and define a device body having a rounded outer periphery and a length greater than its width

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the devices may be disassembled, and any number of the particular pieces or parts of the devices may be selectively replaced or removed in any combination. Upon cleaning and/or replacement of particular parts, some versions of the devices may be reassembled for subsequent use either at a reconditioning facility, or by a user immediately prior to a procedure. Those skilled in the art will appreciate that reconditioning of a devices may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue compression device for forming an anastomosis between first and second anatomical structures, the device comprising:
   (a) a first device portion having a first elongate body defining a first mating surface and a first convex outer surface opposed from the first mating surface and extending longitudinally along the length of the first elongate body; and
   (b) a second device portion having a second elongate body defining a second mating surface and a second convex outer surface opposed from the second mating surface and extending longitudinally along the length of the second elongate body, wherein the second mating surface is configured to mate with the first mating surface to compress tissue positioned therebetween to induce necrosis of the compressed tissue,
   wherein the first and second convex outer surfaces are configured to oppose one another and cooperate to define a rounded outer periphery of the tissue compression device,
   wherein each of the first and second mating surfaces includes a contoured portion that extends longitudinally along a length of the respective first or second elongate body,
   wherein the contoured portions are configured to mate with one another to facilitate alignment of the first and second device portions, wherein the first and second device portions are configured to magnetically attract one another to compress tissue positioned between the first and second mating surfaces.

2. The tissue compression device of claim 1, wherein the contoured portion of the first mating surface is shaped with a first contour that complements a second contour of the contoured portion of the second mating surface.

3. The tissue compression device of claim 2, wherein one of the contoured portions is shaped with a concave contour and the other of the contoured portions is shaped with a complementary convex contour.

4. The tissue compression device of claim 1, wherein each of the first and second mating surfaces includes a first contoured portion shaped with a first radius of curvature and a second contoured portion shaped with a differing second radius of curvature.

5. The tissue compression device of claim 4, wherein the first radius of curvature of the first contoured portion is defined within a first plane and the second radius of curvature of the second contoured portion is defined within a second plane orthogonal to the first plane.

6. The tissue compression device of claim 4, wherein the first contoured portion extends along a length of the respective device portion and the second contoured portion extends along a width of the respective device portion.

7. The tissue compression device of claim 1, wherein each of the first and second mating surfaces includes first and second side portions and first and second end portions, wherein the first and second side portions of the first mating surface are configured to mate with the first and second side portions, respectively, of the second mating surface, and the first and second end portions of the first mating surface are configured to mate with the first and second end portions, respectively, of the second mating surface.

8. The tissue compression device of claim 7, wherein the first side portions of the first and second mating surfaces are shaped with complementary contours, and the second side portions of the first and second mating surfaces are shaped with complementary contours.

9. The tissue compression device of claim 8, wherein each of the side portions of the first mating surface is shaped with a concave contour, and each of the side portions of the second mating surface is shaped with a convex contour that complements the concave contour of the corresponding side portion of the first mating surface.

10. The tissue compression device of claim 7, wherein the first end portions of the first and second mating surfaces are shaped with complementary contours, and the second end portions of the first and second mating surfaces are shaped with complementary contours.

11. The tissue compression device of claim 10, wherein each of the end portions of the first mating surface is shaped with a concave contour, and each of the end portions of the second mating surface is shaped with a convex contour that complements the concave contour of the corresponding end portion of the first mating surface.

12. The tissue compression device of claim 7, wherein each of the side portions of the first and second mating surfaces is shaped with a first radius of curvature, and each of the end portions of the first and second mating surfaces is shaped with a differing second radius of curvature.

13. The tissue compression device of claim 7, wherein the first and second side portions of each of the mating surfaces extend in directions parallel to one another.

14. The tissue compression device of claim 1, wherein each of the first and second mating surfaces includes first and second contoured side portions and first and second contoured end portions.

15. The tissue compression device of claim 1, wherein the first and second elongate bodies are configured to cooperate to provide the tissue compression device with a spherocylindrical exterior.

16. A tissue compression device for forming an anastomosis between first and second anatomical structures, the device comprising:
   (a) a first device portion having a first elongate body defining a first mating surface; and
   (b) a second device portion having a second elongate body defining a second mating surface configured to mate with the first mating surface, wherein the first and second device portions are configured to magnetically draw together to compress tissue positioned between the first and second mating surfaces to induce necrosis of the compressed tissue;

wherein at least a portion of the first mating surface is concavely contoured in a direction away from the second mating surface, wherein at least a portion of the second mating surface is convexly contoured in a direction toward the first mating surface, wherein each of the concavely contoured portion and the convexly contoured portion extends longitudinally along a length of the respective first or second elongate body, wherein the first and second elongate bodies are configured to cooperate to provide the tissue compression device with a convexly rounded cross-sectional profile taken transversely to a length of the tissue compression device, wherein the convexly rounded cross-sectional profile is uniform along a length of a medial portion of the tissue compression device, wherein the convexly rounded cross-sectional profile is intersected by the first and second mating surfaces.

17. The tissue compression device of claim 16, wherein each of the first and second mating surfaces includes first and second contoured side portions and first and second contoured end portions.

18. The tissue compression device of claim 16, wherein the convexly rounded cross-sectional profile comprises a circular cross-sectional profile.

19. A tissue compression device for forming an anastomosis between first and second anatomical structures, the device comprising:

(a) a first device portion including a unitary body having a first mating surface and a continuously rounded outer periphery extending between first and second side portions of the first mating surface;

(b) a second device portion including a unitary body having a second mating surface and a continuously rounded outer periphery extending between first and second side portions of the second mating surface;

(c) a first magnetic member supported by the first device portion; and (d) a second magnetic member supported by the second device portion;

wherein the first and second magnetic members are configured to draw the first and second device portions together to compress tissue between the first and second mating surfaces to induce necrosis of the compressed tissue, wherein the first and second device portions are configured to combine to define a device body having a rounded outer periphery, a length greater than a width of the device body, a cross-sectional profile formed by the continuously rounded outer periphery of the first device portion and the second device portion that is intersected by the first and second mating surfaces, and an interior cavity, wherein the first and second mating surfaces extend about an outer perimeter of the interior cavity.

* * * * *